(12) United States Patent
Wu et al.

(10) Patent No.: US 9,205,248 B2
(45) Date of Patent: Dec. 8, 2015

(54) SAFETY DRUG DELIVERY CONNECTORS

(75) Inventors: Yongxian Wu, Wayne, NJ (US); Yun Jin, Morristown, NJ (US); Mitali Aon, Princeton Junction, NJ (US); Michael D. Garrison, Sparta, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 12/711,641

(22) Filed: Feb. 24, 2010

(65) Prior Publication Data
US 2011/0208128 A1    Aug. 25, 2011

(51) Int. Cl.
| | | |
|---|---|---|
| *A61M 5/00* | (2006.01) |
| *E03B 1/00* | (2006.01) |
| *A61M 39/24* | (2006.01) |
| *A61J 1/20* | (2006.01) |
| *A61M 39/26* | (2006.01) |

(52) U.S. Cl.
CPC ............... *A61M 39/24* (2013.01); *A61J 1/201* (2015.05); *A61J 1/2037* (2015.05); *A61J 1/2051* (2015.05); *A61J 1/2096* (2013.01); *A61M 39/26* (2013.01); *A61J 2001/201* (2013.01); *A61J 2001/2037* (2013.01); *A61J 2001/2051* (2013.01); *A61M 2039/248* (2013.01); *A61M 2039/261* (2013.01)

(58) Field of Classification Search
CPC .......... A61J 1/2096; A61J 2001/2037; A61M 2039/248; A61M 39/24; A61M 39/26
USPC ............... 604/30, 31, 33, 246, 247, 249, 256, 604/533, 534, 535, 537, 538, 539, 905; 251/149.6
See application file for complete search history.

(56) References Cited

U.S. PATENT DOCUMENTS

| | | | |
|---|---|---|---|
| 3,557,778 A * | 1/1971 | Hughes ................ | A61B 5/1438 600/577 |
| 3,570,484 A | 3/1971 | Steer | |
| 4,038,983 A * | 8/1977 | Mittleman ............ | F16K 15/147 417/435 |
| 4,103,686 A * | 8/1978 | LeFevre ................ | A61M 5/172 137/211 |
| 4,143,853 A | 3/1979 | Abramson | |

(Continued)

FOREIGN PATENT DOCUMENTS

| | | |
|---|---|---|
| CN | 2484967 | 4/2002 |
| CN | 2724746 | 9/2005 |

(Continued)

OTHER PUBLICATIONS

Correspondence, *British Journal of Anaesthesia* 86(6) 2001, 896-904.

(Continued)

*Primary Examiner* — Nicholas Lucchesi
*Assistant Examiner* — Gerald Landry, II
(74) *Attorney, Agent, or Firm* — Servilla Whitney LLC

(57) ABSTRACT

Drug delivery connectors are provided for permitting and blocking fluid flow between a container and a catheter connector or other drug delivery site. Embodiments of the drug delivery connectors include a ball valve for forming a releasable seal within the drug delivery connectors. In one or more embodiments, the ball valve prevents fluid flow between an open proximal end and an open distal end of the drug delivery connector and is movable in a proximal direction to release the releasable seal to permit fluid flow from the open proximal direction to the open distal direction. Methods of delivering medication to a catheter connector that includes an actuator are also provided.

13 Claims, 23 Drawing Sheets

(56) References Cited

U.S. PATENT DOCUMENTS

| | | | |
|---|---|---|---|
| 4,336,036 A | 6/1982 | Leeke et al. | |
| 4,387,879 A | 6/1983 | Tauschinski | |
| 4,485,014 A | 11/1984 | Gilroy et al. | |
| 4,621,654 A * | 11/1986 | Holter | A61M 27/006 137/38 |
| 4,683,916 A | 8/1987 | Raines | |
| 4,740,205 A | 4/1988 | Seltzer et al. | |
| 4,838,875 A | 6/1989 | Somor | |
| 5,069,225 A | 12/1991 | Okamura | |
| 5,100,394 A | 3/1992 | Dudar et al. | |
| 5,190,067 A | 3/1993 | Paradis et al. | |
| 5,349,984 A | 9/1994 | Weinheimer et al. | |
| 5,376,073 A | 12/1994 | Graves et al. | |
| 5,390,898 A | 2/1995 | Smedley et al. | |
| 5,437,648 A | 8/1995 | Graves et al. | |
| 5,437,650 A | 8/1995 | Larkin et al. | |
| 5,465,938 A | 11/1995 | Werge et al. | |
| 5,484,421 A | 1/1996 | Smocer | |
| 5,496,274 A | 3/1996 | Graves et al. | |
| 5,509,911 A | 4/1996 | Cottone, Sr. et al. | |
| 5,520,665 A | 5/1996 | Fleetwood | |
| 5,535,785 A | 7/1996 | Werge et al. | |
| 5,573,516 A | 11/1996 | Tyner | |
| 5,584,314 A | 12/1996 | Bron | |
| 5,616,133 A | 4/1997 | Cardenas | |
| 5,616,136 A | 4/1997 | Shillington et al. | |
| 5,749,861 A | 5/1998 | Guala et al. | |
| 5,755,709 A | 5/1998 | Cuppy | |
| 5,775,671 A | 7/1998 | Cote, Sr. | |
| 5,817,063 A | 10/1998 | Turnbull | |
| 5,827,429 A | 10/1998 | Ruschke et al. | |
| 5,968,020 A | 10/1999 | Saito | |
| 6,050,957 A * | 4/2000 | Desch | 600/579 |
| 6,050,978 A | 4/2000 | Orr et al. | |
| 6,096,024 A | 8/2000 | Graves et al. | |
| 6,261,266 B1 | 7/2001 | Jepson et al. | |
| 6,273,870 B1 | 8/2001 | Garvin | |
| 6,402,207 B1 | 6/2002 | Segal et al. | |
| 6,428,514 B1 | 8/2002 | Goebel et al. | |
| 6,500,153 B1 | 12/2002 | Sheppard et al. | |
| 6,544,235 B2 | 4/2003 | Motisi et al. | |
| 6,579,263 B1 * | 6/2003 | Chernack | A61M 5/007 604/131 |
| 6,605,076 B1 | 8/2003 | Jepson et al. | |
| 6,612,624 B1 | 9/2003 | Segal et al. | |
| 6,988,510 B2 | 1/2006 | Enerson | |
| 7,040,598 B2 | 5/2006 | Raybuck | |
| 7,137,654 B2 | 11/2006 | Segal et al. | |
| 7,291,133 B1 * | 11/2007 | Kindler | A61M 5/36 604/247 |
| 7,306,566 B2 | 12/2007 | Raybuck | |
| 7,651,481 B2 | 1/2010 | Raybuck | |
| 2003/0018301 A1 | 1/2003 | Sheppard et al. | |
| 2003/0032940 A1 | 2/2003 | Doyle | |
| 2004/0201216 A1 | 10/2004 | Segal et al. | |
| 2004/0254542 A1 * | 12/2004 | Sacco | A61M 5/14 604/247 |
| 2005/0087715 A1 * | 4/2005 | Doyle | A61M 39/045 251/149.1 |
| 2006/0027270 A1 | 2/2006 | Truitt et al. | |
| 2006/0033331 A1 | 2/2006 | Ziman | |
| 2006/0237065 A1 | 10/2006 | Enerson | |
| 2007/0016161 A1 | 1/2007 | Costa et al. | |
| 2007/0179454 A1 | 8/2007 | Ziman et al. | |
| 2007/0260195 A1 | 11/2007 | Bartholomew et al. | |
| 2008/0045929 A1 | 2/2008 | Birnbach | |
| 2008/0058702 A1 | 3/2008 | Arndt et al. | |
| 2008/0103486 A1 | 5/2008 | Owens | |
| 2008/0139950 A1 | 6/2008 | Molnar et al. | |
| 2008/0140020 A1 | 6/2008 | Shirley | |
| 2008/0140055 A1 | 6/2008 | Shirley | |
| 2008/0312640 A1 | 12/2008 | Grant | |
| 2008/0318456 A1 | 12/2008 | Yow et al. | |
| 2008/0319422 A1 * | 12/2008 | Cardenas | 604/537 |
| 2009/0099552 A1 | 4/2009 | Levy et al. | |
| 2009/0187166 A1 | 7/2009 | Young | |
| 2010/0286558 A1 | 11/2010 | Schraga | |
| 2011/0208160 A1 | 8/2011 | Wu et al. | |

FOREIGN PATENT DOCUMENTS

| | | |
|---|---|---|
| EP | 1233809 B1 | 9/2004 |
| GB | 2270725 | 3/1994 |
| JP | 2003-126269 | 5/2003 |
| JP | 2003-339876 | 12/2003 |
| WO | WO 03/018105 | 3/2003 |
| WO | WO-2006/020635 A2 | 2/2006 |
| WO | WO-2007/089531 A2 | 8/2007 |

OTHER PUBLICATIONS

Anderson, MD, Ronald A. "Letter to the Editor: Infallible Measures Needed to Prevent Errors in the Administration of Chemotherapeutic Agents", *Medical and Pediatric Oncology* 32 1999, 401-402.

Katz, Leon "Inadvertent Misconnection of Medical Tubing: Protective Incompatibility", *Health and Welfare* Canada, Ottawa 1986, 2517-2518.

Lanigan, "Correspondence", *Anesthesia*, 56 2001, 585-610.

Toft, Prof., Brian "External Inquiry into the adverse incident that occurred at Queen's Medical Centre, Nottingham", *Department of Health* Jan. 4, 2001, 70 pgs.

Woods, Prof., Kent W. "The Prevention of Intrathecal Medication Errors—A report to the Chief Medical Officer", *Department of Healt* Apr. 2001, 20 pgs.

Stabile, Mike, et al. "Medication Administration in Anesthesia", http:www.apsf.org/resource_center/newsletter/2007/fall/02_medicaladministration.htm, Dec. 10, 2009, 6 pgs.

Sheppard, Ian, et al., "Medication Safety Alerts", *JCPH*, vol. 57, Jun. 2004, 176-179.

Non-Final Office Action in U.S. Appl. No. 12/711,805, mailed Apr. 11, 2011, 15 pgs.

Final Office Action in U.S. Appl. No. 12/711,805, mailed Oct. 12, 2011, 15 pgs.

PCT International Search Report & Written Opinion in PCT/US2011/045281, mailed Apr. 19, 2012, 23 pgs.

Non-Final Office Action in U.S. Appl. No. 12/844,546, dated Jun. 25, 2012, 24 pgs.

Non-Final Office Action in U.S. Appl. No. 12/711,805, dated Dec. 20, 2013, 17 pages.

PCT International Search Report in PCT/US2011/025858, dated May 27, 2011, 2 pgs.

PCT IPRP & Written Opinion in PCT/US2011/025858, dated Aug. 28, 2012, 8 pgs.

Final Office Action in U.S. Appl. No. 12/711,805, dated Sep. 25, 2014, 16 pages.

\* cited by examiner

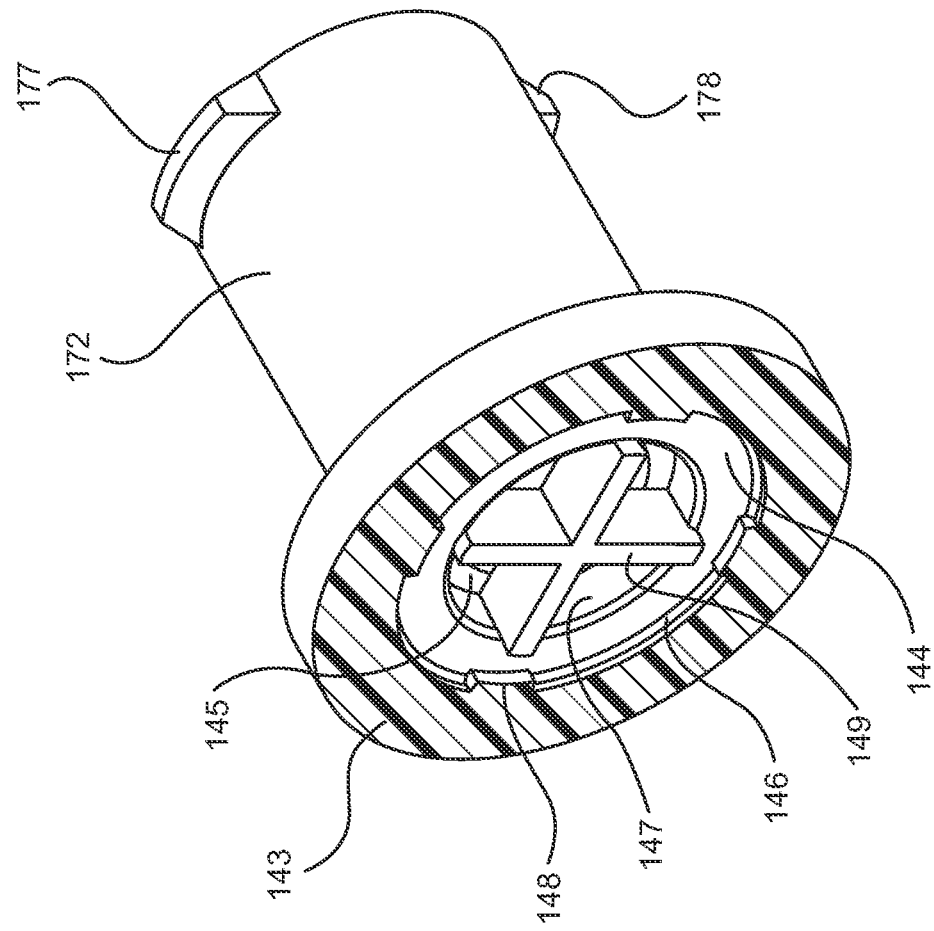
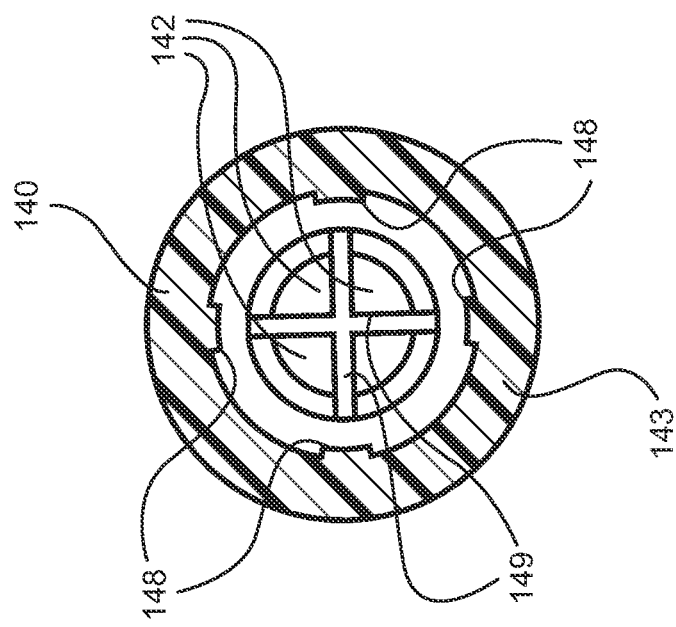
FIG. 14A
FIG. 14

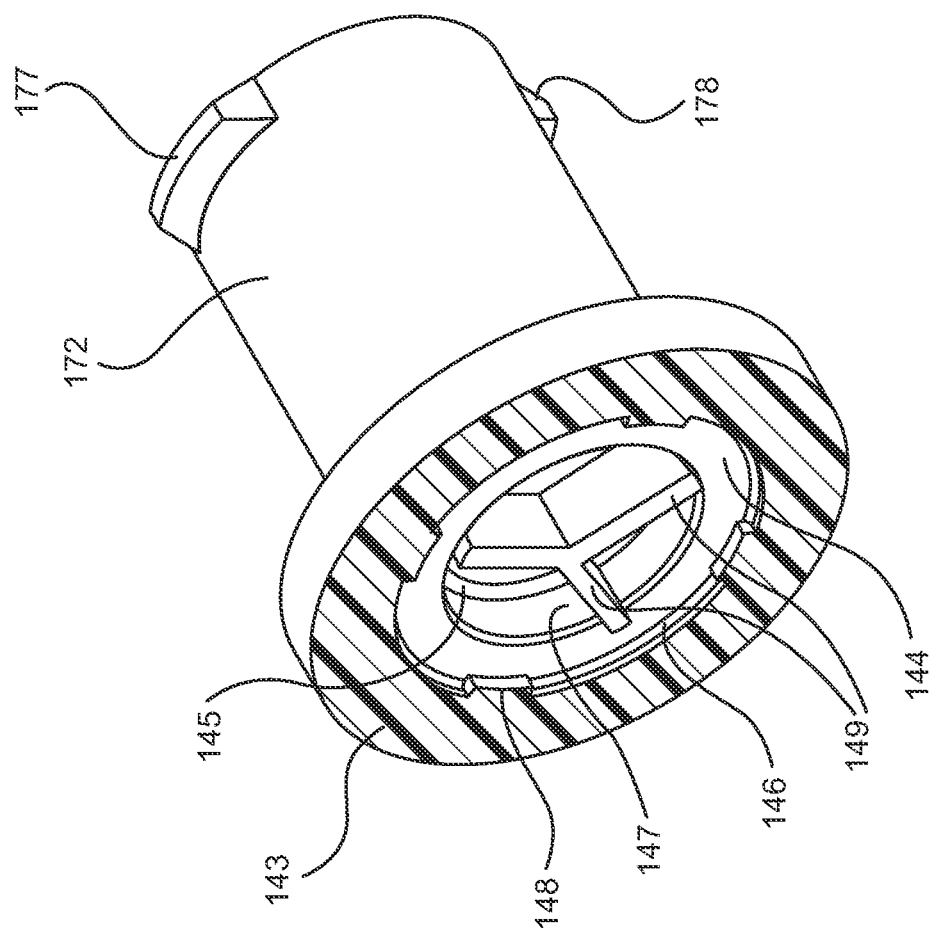
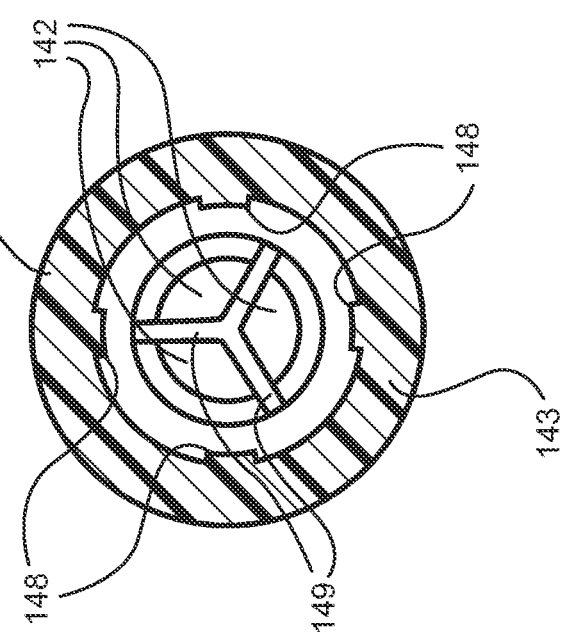

SAFETY DRUG DELIVERY CONNECTORS

TECHNICAL FIELD

Aspects of the present invention relate to drug delivery connectors that prevent administration of medication to incorrect delivery ports and methods of using the drug delivery connectors.

BACKGROUND

Drug delivery devices typically share a common ISO standard luer connection, including intravascular, anesthesia and enteral delivery devices. Misconnections of these routes are possible and will cause medication error. The consequences of such errors may be adverse or even fatal.

Previous attempts at reducing errors in drug delivery include the use of labels or color coded devices to differentiate specific route-accessing devices (e.g., catheter connectors) and drug-containing devices or containers for retaining medication (e.g., syringe barrels). Studies have shown that clinicians tend to ignore these labels and color codes. Other attempts to reduce error have required the use of valves with containers to prevent accidental connection and delivery. The operation of such valves often requires additional components to open the valve and/or secure attachment of the valve to the container that can be cumbersome for attachment and use. The use of some of these additional components to open the valve and/or secure attachment of the valve to the container, such a syringe barrels, has also required the use of specialized syringe and/or catheter connections. In specific instances, the valves may have complex structures that are difficult to manufacture and utilize and/or may utilize large surface areas on which meniscus may form between the valve and the wall of the surrounding container within which the drug is stored. Further, the large surface area of the valves provides an increased opportunity for microbial growth, which may cause infection. In addition, typical valves are opened in the direction of the fluid flow and/or are opened by the containers that retain medication to be dispensed. For example, conventional valves may be opened by attaching a push rod to a syringe barrel filled with mediation. The push rod activates the check valve in the direction of the fluid flow (from the syringe barrel or other fluid or liquid container). In these configurations the syringe barrel cannot be attached to a standard hypodermic needle, which makes is impossible to pre-attach the push rod connector to the syringe. Further, such valves are generally intended to prevent fluid flow back and could contaminate the medication source.

All of these issues could lead to the malfunction of the valve and drug delivery procedure. In addition, the known devices do not allow the user to remove air from the container. Accordingly, there is a need for a drug delivery connector that can effectively eliminate all wrong-route medication error possibilities for use in a variety of drug delivery procedures with standard syringes and other drug-containing devices. Further, there is a need for a drug delivery connector that permits normal aspiration of medication into a container and air priming, while providing a valve that prevents leakage of the aspirated medication.

SUMMARY

In this disclosure, a convention is followed wherein the distal end of the device is the end closest to a patient and the proximal end of the device is the end away from the patient and closest to a practitioner.

A first aspect of the present invention pertains to a drug delivery connector including a ball valve. In one or more embodiments, the drug delivery connector comprises a housing including an open distal end, an open proximal end and defining a chamber in fluid communication with the open distal end and the open proximal end. The housing may also include a proximal connection portion for attaching the housing to a container and a distal connection portion. The distal connection portion and/or the proximal connection portion may include a luer lock fitting or a luer slip fitting. The ball valve is disposed within the chamber and forms a releasable seal with the open distal end of the drug delivery connector to prevent fluid flow from the open proximal end of the housing to the open distal end of the housing.

The housing also includes a structure for forming one or more fluid flow paths around the ball valve. The structure may be a longitudinal protrusion, a rib, an expanding sidewall and/or combinations thereof. The chamber of the housing may also include a retaining ring that inhibits movement of the ball valve within the chamber in the proximal direction.

The housing of one or more embodiments may also include a proximal wall disposed adjacent to the open proximal end of the drug delivery connector. The proximal wall includes at least one aperture allowing constant fluid communication between the open proximal end and the chamber of the housing. The housing may also include a distal wall disposed adjacent to the open distal end of the drug delivery connector that includes a bore having a perimeter that is configured to contact the ball valve to form a releasable seal between the ball valve and the distal wall.

In one or more embodiments, the ball valve is moveable in a proximal direction to release the releasable seal formed with the distal wall and to permit fluid flow from the open proximal end to the open distal end upon application of a force in the proximal direction on the ball valve. In a specific embodiment, the ball valve is moveable in a distal direction to form the releasable seal with the distal wall upon application of a force in the distal direction on the ball valve. In accordance with one or more embodiments, the attachment of a container including a fluid to the proximal connection portion of the housing causes the fluid held within the container to apply the force to the ball valve in the distal direction to move the ball valve in the distal direction. The force applied to the ball valve causes the ball valve to form a releasable seal with the open distal end.

In one or more embodiments, the drug delivery connector may include an actuator attachable or for attachment to the open distal end of the housing. The actuator includes an open distal end and a projection extending in the proximal direction from the open distal end. In one or more embodiments, the projection includes at least one open path or aperture in fluid communication with the open distal end of the actuator and the open distal end of the housing. Upon attachment of the actuator to the open distal end of the housing, the projection extends through the bore of the distal wall into the chamber and applies a force on the ball valve in the proximal direction to move the ball valve in the proximal direction. In one or more embodiments, the ball valve is movable in the proximal direction upon application of a minimum or pre-determined force on the ball valve in the proximal direction. In one or more embodiments, a coil spring or other device may be disposed within the housing to exert a constant force on the ball valve in the distal direction. The spring constant of the coil spring may be adjusted or selected to select the minimum or pre-determined force required to release the seal between the ball valve and the distal wall.

In accordance with a second aspect of the present invention, the drug delivery connector includes a housing including an open distal end, an open proximal end and a chamber in fluid communication with the open distal end and the open proximal end, means for attaching the housing to a catheter connector comprising an actuator, means for attaching the housing to a container and means for permitting and blocking fluid communication between the container and the catheter connector from the open proximal end to the open distal end. In one or more embodiments, the means for permitting and blocking fluid communication comprises a ball valve. In a specific embodiment, the means for permitting and blocking fluid communication comprises a spring-loaded ball valve.

A third aspect of the present invention pertains to a method of delivering liquid medication to a catheter connector. In one or more embodiments, the method includes attaching an actuator, as described herein, to a catheter, providing a drug delivery connector a housing with an open distal end, an open proximal end and a chamber with a valve, as described herein, in fluid communication with the open distal end and open proximal end of the housing, attaching a tip of a syringe barrel to the open proximal end of a drug delivery connector, filling the syringe barrel with a pre-determined amount of liquid medication, filling the chamber of the drug delivery connector with the liquid medication to form a seal between the valve and the open distal end and releasing the seal between the valve and the open distal end by attaching the open distal end to the actuator. In one or more embodiments, the actuator includes a projection with a length that extends into the chamber of the housing. The projection may include an aperture or open path in fluid communication with the catheter connector. The step of releasing the seal between the valve and the open distal end may include causing the projection of the actuator to apply a force to the valve in a proximal direction. In one or more embodiments, the step of releasing the seal between the valve and the open distal end permits the liquid medication to flow from the chamber to the aperture or open path of the projection.

BRIEF DESCRIPTION OF THE DRAWINGS

FIG. 14 shows the proximal end of the drug delivery connector shown in FIG. 13 including a proximal wall according to one or more embodiments of the present invention;

FIG. 14A shows a perspective view of the drug delivery connector shown in FIG. 14;

FIG. 15 shows the proximal end of the drug delivery connector shown in FIG. 13 including a proximal wall according to one or more embodiments of the present invention;

FIG. 15A shows a perspective view of the drug delivery connector shown in FIG. 15;

DETAILED DESCRIPTION

Figure 1:
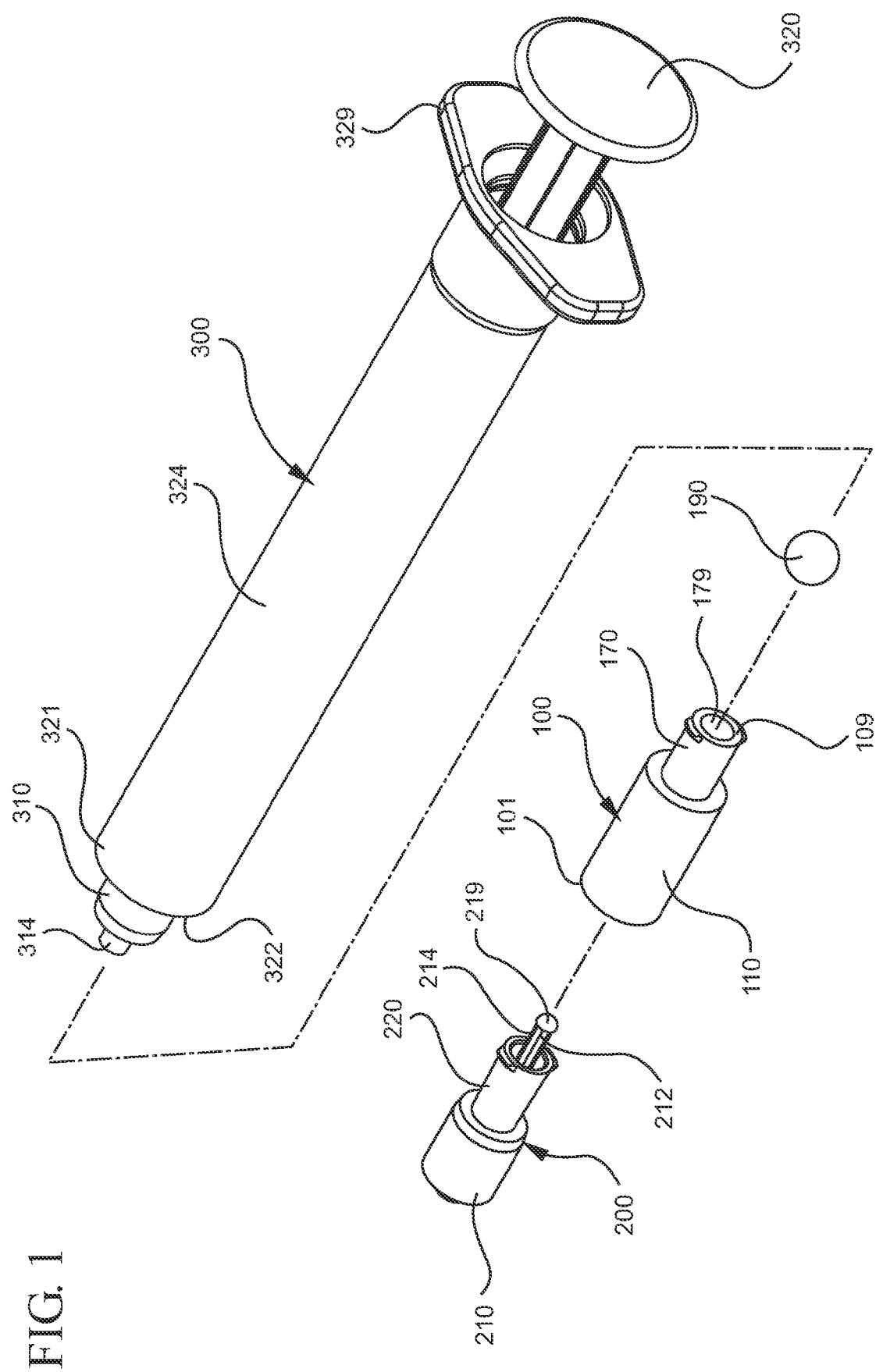
FIG. 1 illustrates a disassembled perspective view of one or more embodiments of the drug delivery connector shown with a syringe barrel and a actuator.
Figure 2:
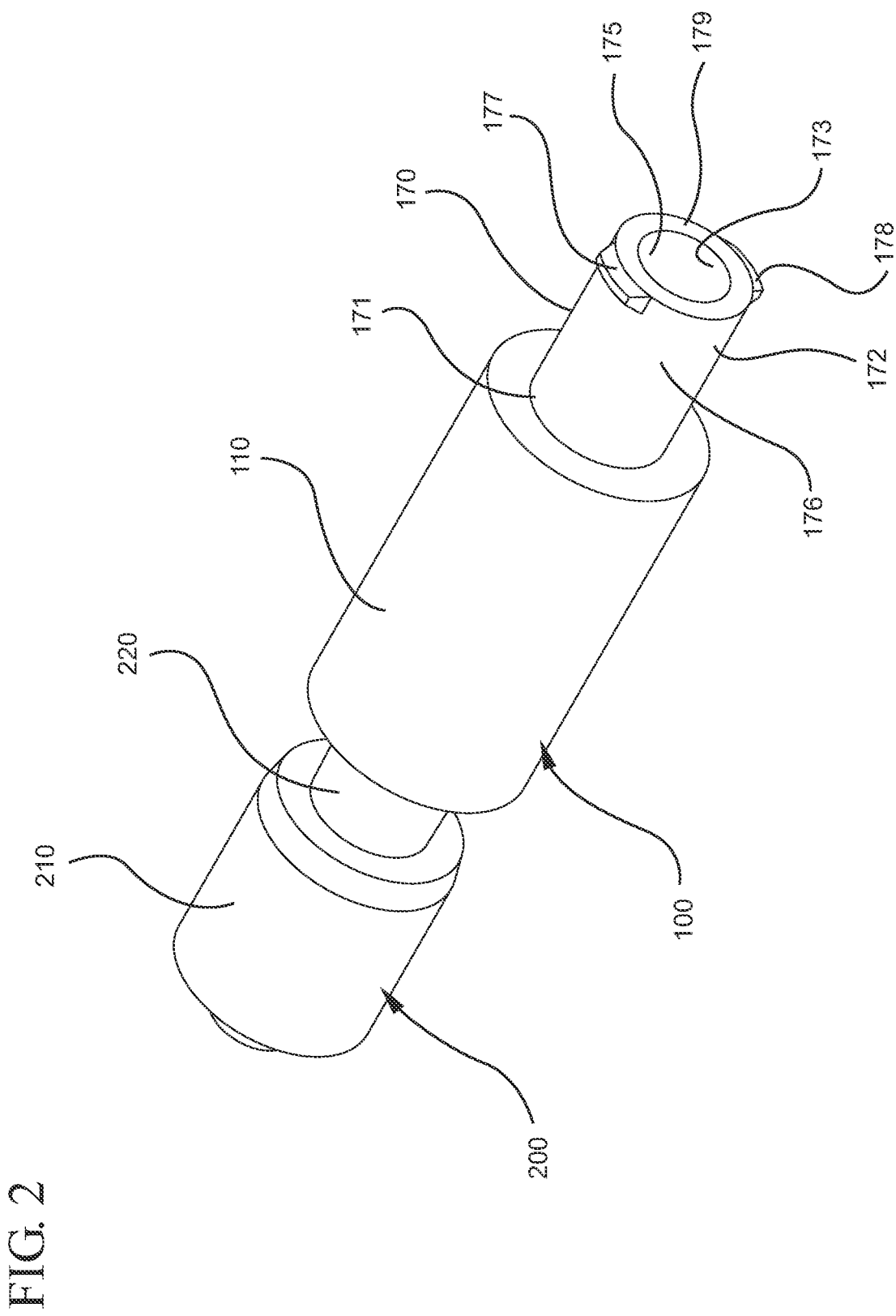
FIG. 2 illustrates an perspective view of the drug delivery connector shown in FIG. 1 assembled with the actuator.
Figure 3:
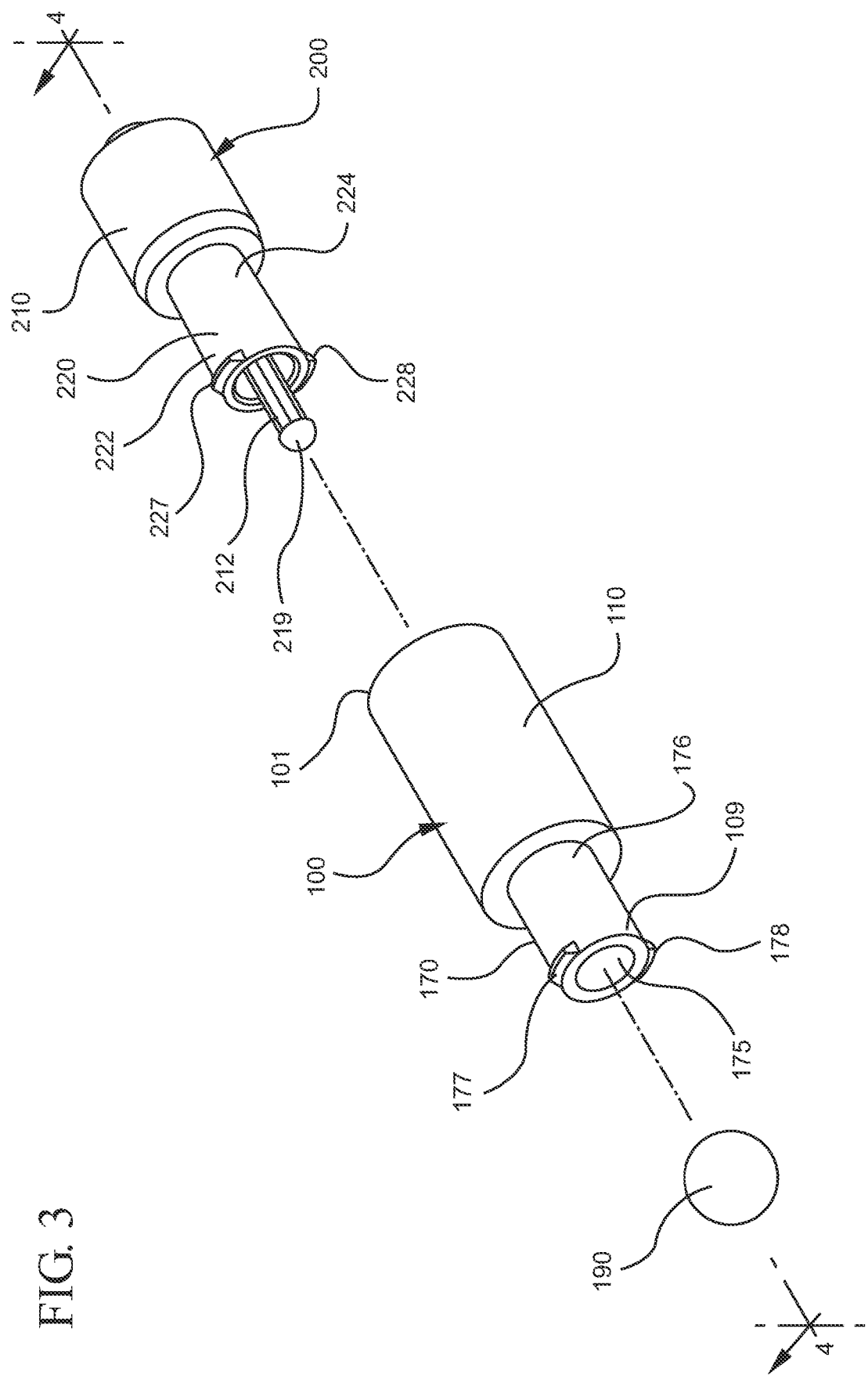
FIG. 3 illustrates an enlarged view of the drug delivery connector and actuator shown in FIG. 1.

Before describing several exemplary embodiments of the invention, it is to be understood that the invention is not limited to the details of construction or process steps set forth in the following description. The invention is capable of other embodiments and of being practiced or being carried out in various ways.

Aspects of the present invention pertain to drug delivery connectors. The drug delivery connectors may be utilized for delivery of medication from a container to delivery site for delivery to a patient intravenously or via epidural space. Exemplary containers include syringe barrels, IV bag or other medical devices used to store, transport and/or delivery anesthesia. In one or more embodiments, the drug delivery connector provides a fluid-tight connection mechanism between a delivery site and a container. In a specific embodiment, the drug delivery connector provides a fluid-tight connection mechanism between a catheter connector or other delivery site and a syringe barrel. The fluid-tight connection mechanism between a delivery site and a drug container may include a filter. Examples of connection mechanisms utilized to connect a delivery site and syringe barrel to the drug delivery connectors described herein include standard luer slip connections or standard luer lock connections. The drug delivery connectors described herein include a structure to prevent flow of medication from the container when attached to an inappropriate delivery site and permit flow of medication from the container when attached to an appropriate delivery site.

In accordance with one or more embodiments, the drug delivery connector includes a ball valve disposed in the flow path of the medication from a container to a delivery site. The ball valve of one or more embodiments forms a one-way valve or a check valve. As used herein, the term "one-way valve" includes any valves which permit fluid flow in one direction. As used herein, the terms "check valve" may be used interchangeably with the term "one-way valve." In a specific embodiment, the ball valve is activated or opened by an actuator, which may be in the form of a push rod and may not be activated or opened by the container or even the delivery site. In a more specific embodiment, the ball valve is activated by the actuator, which may include a catheter connector for connection of the drug delivery connector and container to a catheter or other delivery site. The ball valve prevents fluid flow across the drug delivery connector from the container to the actuator and, thus, the delivery site. The ball valve permits the user to attach the drug delivery connector to at least one of the container and/or actuator without accidental expulsion of medication from the container. Further the drug delivery connector may be used with containers without fear of leakage or accidental administration of the medication contained therein.

A drug delivery connector 100 according to a first aspect is shown in FIGS. 1-6. As shown more clearly in FIGS. 4-6, the drug deliver connector 100 includes an open distal end 101 and an open proximal end 109. The drug delivery connector includes a housing 110, a distal connection portion 150 extending from the housing 110 to the open distal end 101 of the drug delivery connector and a proximal connection portion 170 extending from the housing 110 to the open proximal end 109 of the drug delivery connector. The distal connection portion 150 is in fluid communication with the housing 110 and the proximal connection portion 170.

For illustration in FIGS. 1-6, a container in the form of a syringe barrel 300 is utilized with the drug delivery connector 100, although the drug delivery connector according to one or more embodiments may also be utilized with other types of containers, for example, an IV bag. In addition, an actuator 200 including a catheter connector 210 is also included for illustration.

Figure 4:
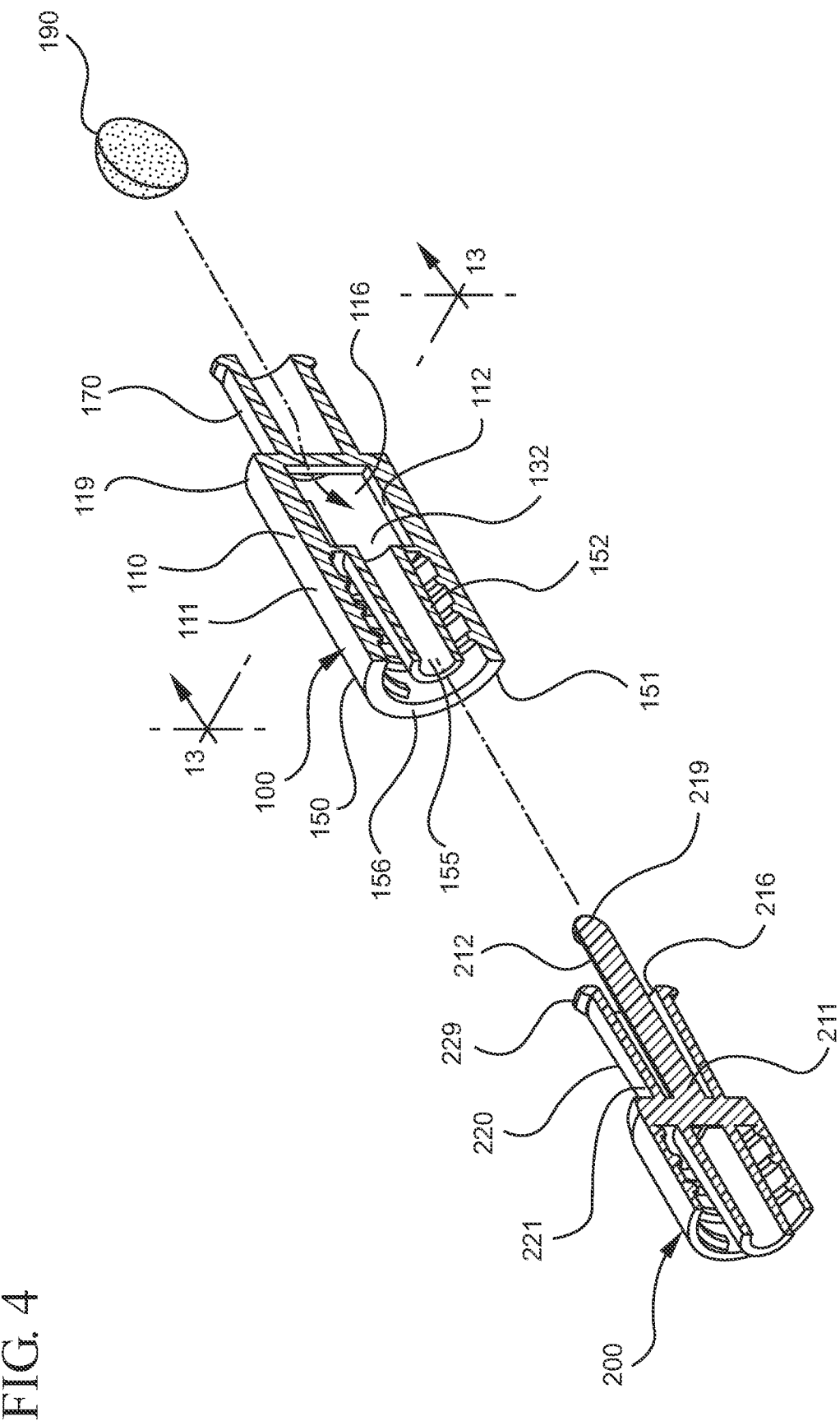
FIG. 4 illustrates a perspective cross-sectional view of the drug delivery connector and actuator shown in FIG. 3 taken along line 4-4 from the view point of the distal end of the drug delivery connector and actuator.
Figure 5:
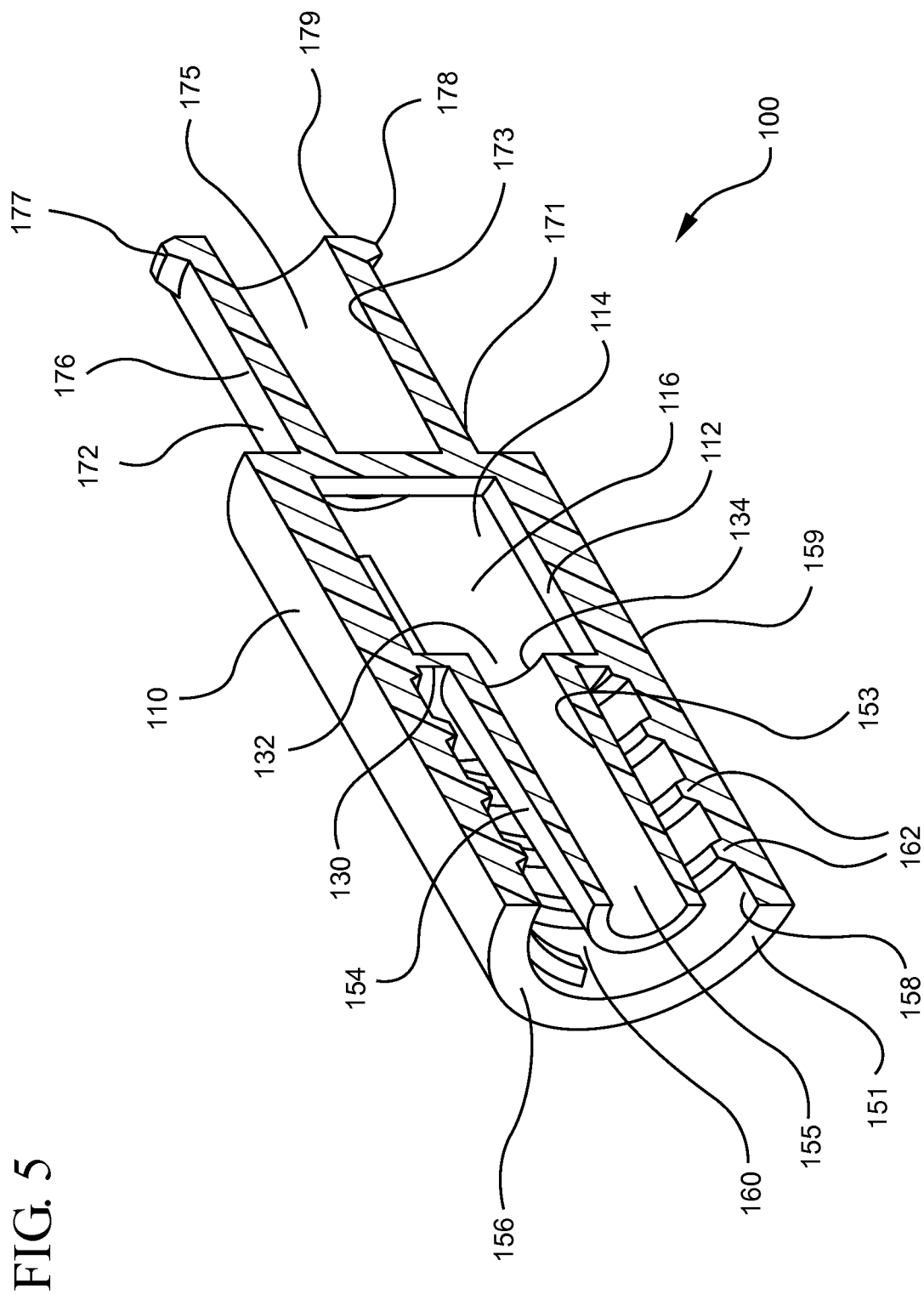
FIG. 5 shows a perspective cross-sectional view of the drug delivery connector shown in FIG. 4.

As more clearly shown in FIGS. 4-5, the distal connection portion 150 includes a distal end 151 and a proximal end 159 including a distal luer fitting for attaching the actuator 200 to the drug delivery connector. In one or more embodiments, the distal connection portion 150 of one or more embodiments may include a fitting in the form of a luer slip fitting (not shown) for connection to an actuator 200. In the embodiment shown in FIGS. 1-6, the distal connection portion 150 includes a fitting in the form of a luer lock fitting including an elongate tube 152 in fluid communication with the housing 110 and extending from the housing 110 to the open distal end 101 of the drug delivery connector. The elongate tube 152 includes an outside surface 154 and a coaxial wall 156 surrounding the elongate tube 152 and defining an inside surface 158 that forms a channel 160 between the inside surface 158 of the coaxial wall 156 and the elongate tube 152. In one or more embodiments, the inside surface 158 of the coaxial wall 156 includes a threaded portion 162 for engaging the actuator 200. The elongate tube includes an inside surface 153 defining a passageway 155 for receiving the actuator 200 (as shown more clearly in FIG. 4). The actuator 200 is shown in FIGS. 1-4 and 20-22 is an example of one or more suitable actuators for activating the ball valve 190 and includes catheter connector 210 for attachment of the actuator 200 to a filter system, catheter or other delivery site. In use, the actuator 200 is inserted into the passageway 155 of the distal connection portion 150 of the drug delivery connector. As will be described in further detail below, the actuator 200 may also include a corresponding structure that allows the actuator 200 to be threaded with the threaded portion 162 of the distal connection portion 150 of the drug delivery connector 100. In one or more embodiments, the flow rate of the medication flowing from the container through the drug delivery connector 100 and to the actuator 200 may be modified or controlled by controlling the level of engagement between the actuator 200 and the drug delivery connector 100. In one or more specific embodiments, the flow rate may be controlled by controlling the amount of rotation applied to the actuator 200 with respect to the drug delivery connector 100 during attachment.

Figure 17:
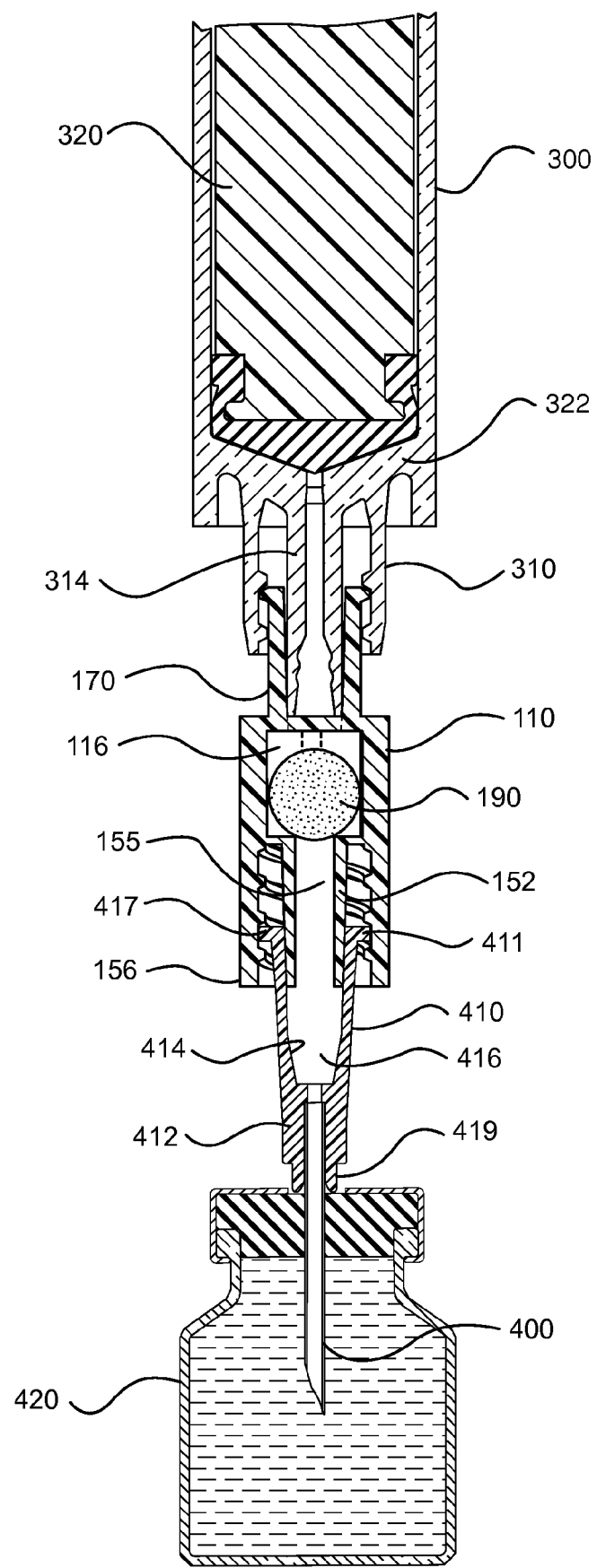
FIG. 17 illustrates a cross-sectional view of a drug delivery connector attached to a syringe barrel and a needle hub positioned with a vial to draw liquid into the syringe barrel.
Figure 18:
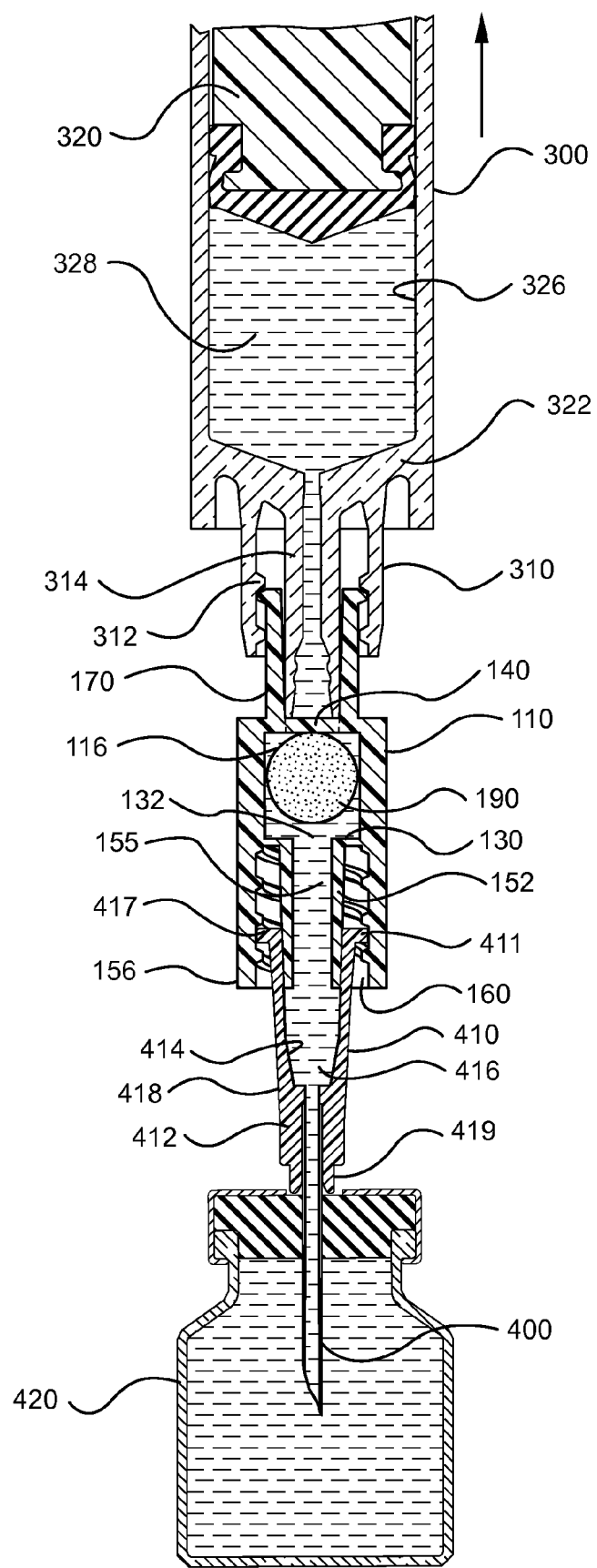
FIG. 18 shows the drug delivery connector, syringe barrel and needle hub shown in FIG. 17 as liquid is being aspirated from the vial into the syringe barrel.

As shown in the embodiment in FIGS. 4-5, the proximal connection portion 170 of the drug delivery connector extends from the housing 110 toward the open proximal end 109 of the drug delivery connector 100. The proximal connection portion 170 includes a proximal luer fitting in the form of an elongate hollow body 172 having an open distal end 171, an open proximal end 179 and an inside surface 173 defining an interior 175 for receiving and engaging an opening of a container, for example, an open tip 314 of the syringe barrel 300 shown in FIG. 1. In one or more embodiments, the elongate hollow body 172 includes an outside surface 176 with at least one radially outwardly extending ridge 177 disposed adjacent to the open proximal end 179. In the embodiment shown, the elongate hollow body 172 includes two ridges 177, 178 disposed on opposite ends of the proximal end of the elongate hollow body 172. In one or more embodiments, the at least one radially extending ridge 177 may extend radially along a portion of circumference of the open proximal end 179 or the entire circumference of the open proximal end 179. The at least one radially outwardly extending ridge 177 permits assembly of the drug delivery connector 100, and, more specifically, the proximal connection portion 170, to a container, for example, the syringe barrel 300 shown in FIG. 1, which may having a luer lock attachment 310 including the open tip 314 and a threaded section 312 surrounding the open tip 314, as shown in FIGS. 1 and 17-18. To assemble the syringe barrel 300 with a luer lock attachment 310 to the proximal connection portion 170 of the drug delivery connector 100, the open tip 314 is inserted into the open proximal end 179 of the elongate hollow body 172 and the syringe barrel 300 and/or the drug delivery connector 100 is rotated relative to one another. During rotation, the threaded section 312 of the luer lock attachment 310 engages the at least one radially outwardly extending ridge 177. In the embodiment shown in FIG. 18, the threaded section 312 engages both radially outwardly extending ridges 177, 178 of the proximal connection portion 170.

In one or more embodiments, the proximal connection portion 170 may permit connection of the drug delivery connector 100 to a syringe with a luer slip tip (not shown). In such embodiments, the inside surface 173 of the elongate hollow body 172 of the proximal connection portion 170 may have a cross-sectional width that increases along the length of the elongate hollow body 172 from the open distal end 171 toward the open proximal end 179 forming a tapered portion (not shown) that frictionally engages the luer slip tip (not shown) of a syringe barrel. To assemble a syringe barrel having a luer slip tip (not shown) to the proximal connection portion 170 of the drug delivery connector, the luer slip tip (not shown) of the syringe barrel is inserted into the interior 175 of the elongate hollow body 172. A force in the distal direction is applied to the syringe barrel relative to the drug delivery connector 100 until the tapered portion (not shown) of the elongate hollow body 172 and the inside surface 173 prevents further movement of the luer slip tip (not shown) in the distal direction relative to the drug delivery connector 100 and the luer slip tip (not shown) is frictional engaged with the inside surface 173 of the proximal connection portion 170.

The housing 110 includes a sidewall 112 having an axial length and an interior surface 114 defining chamber 116. In one or more embodiments, the chamber 116 is cylindrically shaped and has a distal end 111 in fluid communication with the open distal end 151 of the distal connection portion 150 and a proximal end 119 in fluid communication with the open proximal end 179 of the proximal connection portion 170. In one or more embodiments, the distal end 111 includes a distal wall 130 disposed between the chamber 116 and the distal connection portion 150. The distal wall 130 includes at least one bore 132 therethrough having a perimeter 134 to permit fluid communication between the distal connection portion 150 and the chamber 116. The proximal end 119 includes a proximal wall 140 disposed between the chamber 116 and the proximal connection portion 170. The proximal wall 140 includes at least one aperture 142 to allow fluid communication between the proximal connection portion 170 and the chamber 116. As will be described in more detail below, the proximal wall 140 has a structure to prevent the formation of a seal that closes the aperture 142 or, in other words, structure that maintains fluid communication between a container and the chamber 116 when the container is attached to the drug delivery connector 100.

In the embodiment shown in FIGS. 1-6, the chamber 116 of the housing 110 includes a ball valve 190. As will be described below in more detail, the ball valve 190 cooperates with an actuator 200 to permit fluid communication between the syringe barrel 300, drug delivery connector 100 and a delivery site which may include a catheter (not shown) and/or filter (not shown). The ball valve 190 cooperates with the distal wall 130 to prevent fluid communication between the chamber 116 and the distal connection portion 150 through bore 132. According to one or more embodiments, the ball valve 190 remains closed and prevents fluid communication between the chamber 116 and the distal connection portion 150 when the drug delivery connector 100 is attached to a syringe barrel 300 that is filled with medication because the pressure from the medication contained within the syringe barrel 300 applies a continuous force on the ball valve 190 in the distal direction to close the ball valve 190 against the distal wall 130.

In one or more embodiments, the ball valve 190 is sized to fit within the chamber 116 of the housing 110 and has a solid spherical shape and circular cross-section having a dimension and shape to form a releasable seal with the distal wall 130, thereby closing the bore 132 and preventing fluid communication between the chamber 116 and the distal connection portion 150. The ball valve 190 may be formed from a rubber, plastic, metal or ceramic material or combinations thereof. In one or more specific embodiments, the ball valve 190 may be formed from a synthetic rubber and/or a polyurethane material. In a specific embodiment, the ball valve 190 may be formed from a commonly used plastic or other material and coated with synthetic rubber or other polyurethane-containing materials. The ball valve 190 "floats" or is moveable within the chamber in the proximal and distal direction. Forces such as gravity may cause the ball valve 190 to move in either the proximal or distal direction. Other forces such as fluid pressure may cause the ball valve 190 to close the bore 132 or to move in the distal direction to form a seal with the perimeter 134 of the distal wall 130.

Embodiments of the present invention utilize ball valves 190 with a reduced surface area than other valves known and used in the art. A reduced surface area eliminates the issues regarding movement of the ball valve within the chamber 116 and reduces the possibility of meniscus forming between the ball valve 190 and the chamber 116, which could further inhibit movement of the ball valve 190. The reduced surface area of the ball valve 190 also reduces the possibility of microbials forming on the surface of the ball valve 190, which can be especially problematic when the drug delivery connector 100 is used with implanted medical devices, such as catheters, which may remain implanted for several days at a time. In addition, the spherical shape of ball valve 190 facilitates manipulation of the ball valve 190 and eliminates problems of misalignment of the ball valve 190 within the chamber 116 due to varying forces exerted at different locations of the ball valve 190.

Figure 8:
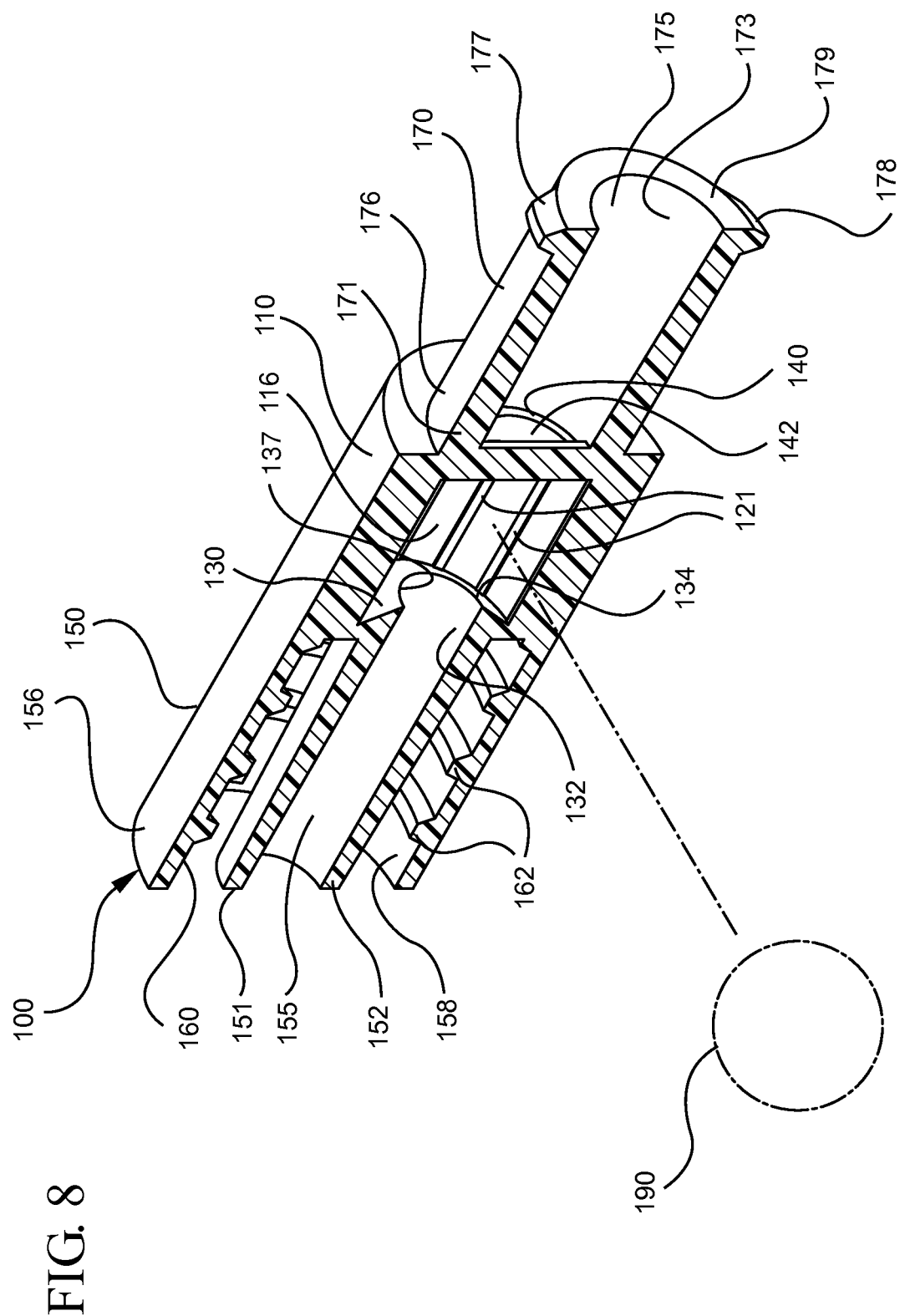
FIG. 8 shows a view of the drug delivery connector shown in FIG. 7 including a distal wall and sidewall according to one or more embodiments of the present invention and a ball valve.

In accordance with one or more embodiments, the ball valve 190 may be spring-loaded. A drug delivery connector including a coil spring 192 disposed within the chamber 116 of the housing 110 is shown in FIG. 8. The coil spring 192 includes a distal end 193 disposed adjacent to the ball valve 190 and a proximal end 194 disposed adjacent to the proximal wall 140. In an inactivated state, the coil spring 192 is expanded, and applies a constant force on the ball valve 190 in the distal direction, forcing the ball valve 190 to remain in contact with the distal wall 130 sealing the bore 132. Other known structures for applying a constant force on the ball valve may also be utilized. To open the ball valve 190, the user would apply a force on the ball valve 190, on the opposite side of the coil spring 192, in the proximal direction. The proximally directed force applied to the ball valve 190 compresses the coil spring 192 and forces the ball valve 190 to move away from the distal wall 130 to permit fluid communication between the chamber 116 of the housing and the bore 132 in the distal wall 130. In one or more embodiments, the spring constant of the coil spring may be adjusted to require a minimum or pre-determined amount of force to activate or open the ball valve.

Figure 6:
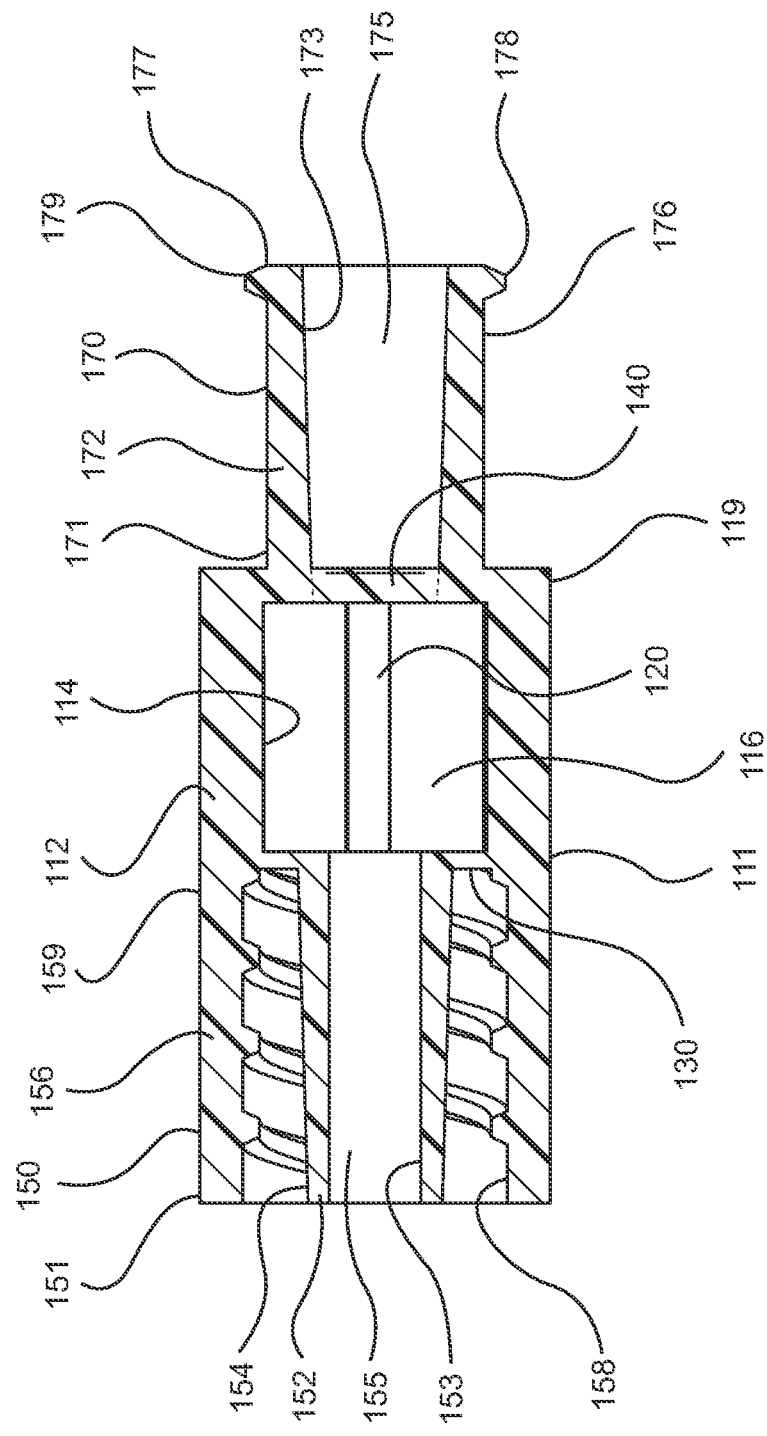
FIG. 6 illustrates side-elevational view of a drug delivery connector shown in FIG. 5.

To form a seal with the bore 132 of the distal wall 130, the ball valve 190 is seated adjacent to the bore 132 and in contact with the distal wall 130. In one or more embodiments, the bore 132 has a cross-sectional width forming a seat that receives the ball valve 190. In one or more embodiments, for example, as shown in FIG. 6, the distal wall 130 is vertically disposed or is disposed perpendicularly to the sidewall 112 of the chamber 116 to form a distal wall 130 having a flat configuration. The contact between the ball valve 190 and the distal wall 130 with a flat configuration may be described as a line contact.

Figure 7:
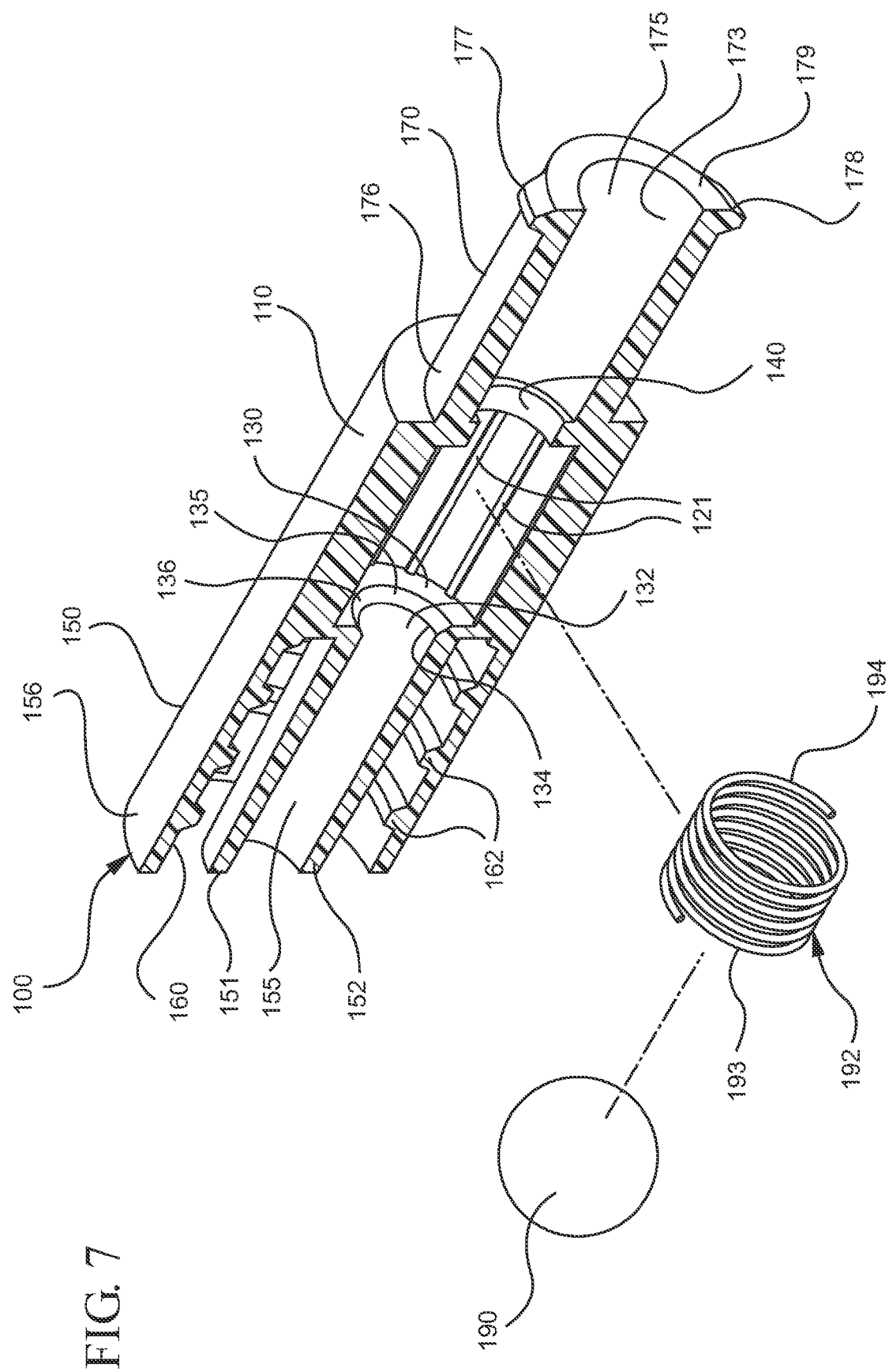
FIG. 7 shows a perspective cross-sectional view of the drug delivery connector shown in FIG. 4 including a distal wall according to one or more embodiments of the present invention, a ball valve and a coil spring.

In a specific embodiment, the distal wall 130 may be contoured adjacent to the perimeter 134 and the bore 132 to further facilitate the formation of a seal between the distal wall 130 and the ball valve 190. In accordance with one or more embodiments, as shown in FIGS. 7 and 8, the distal wall 130 may include a chamfer 135 forming a beveled seat 136 for the ball valve 190. The chamfer 135 allows for a greater surface area of contact between the ball valve 190 and the distal wall 130. In such a configuration, defects or modifications on the surface of the distal wall 130 are not as likely to compromise the seal formed between the ball valve 190 and distal wall 130 as configurations that provide a smaller surface area of contact between the ball valve and the distal wall 130.

Figure 9:
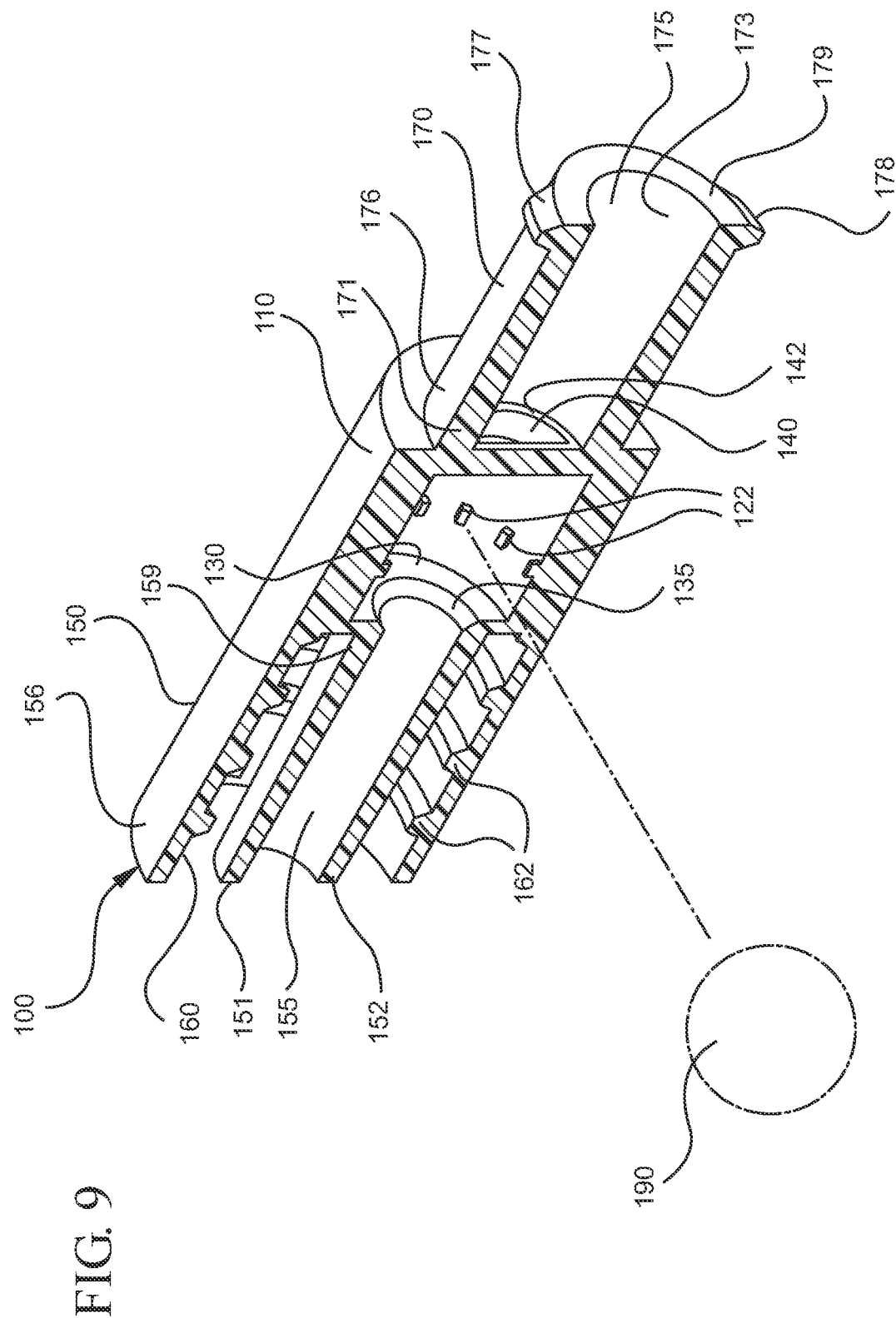
FIG. 9 shows a view of the drug delivery connector shown in FIG. 7 including a distal wall and sidewall according to one or more embodiments of the present invention and a ball valve.

In one or more embodiments, as shown in FIG. 9, the distal wall 130 may extend proximally into the chamber 116 to form a sharp contact point 137 forming a "sharp contact" with the ball valve 190. Sharp contact between the sharp contact point 137 and the ball valve 190 is formed when the distal wall 130 is positioned at an angle of less than 90 degrees relative to the sidewall 112. In other words, during sharp contact between the ball valve 190 and the sharp contact point 137 forms a single line of contact with the ball valve 190. The single line of contact decreases the likelihood of a defect on the distal wall 130 and/or the ball valve 190 will interfere with the formation of a seal. The decreased contact area between the ball valve 190 and the perimeter 134 increases pressure on the ball valve 190 and compresses the ball valve 190. This compression improves the seal formed between the distal wall 130 and the ball valve 190. Compression of the ball valve 190 is particularly pronounced when the ball valve 190 is composed of a softer material or material with smaller elasticity, because it permits dispersal of the force exerted on the ball valve 190, which is not as possible when the ball valve is composed of more rigid materials.

In one or more embodiments, the chamber 116 of the housing 110 may be modified to align the ball valve 190 in the center of the fluid path. For example, in one or more embodiments, the interior surface 114 may include one or more structures or structural features that permit movement of the ball valve 190 in the proximal and distal directions within the chamber 116 but prevent lateral movement of the ball valve 190. In FIG. 6, the interior surface 114 of the sidewall 112 includes at least one longitudinal protrusion 120 extending radially outwardly into the chamber 116 of the housing 110. The longitudinal protrusion 120 defines a smaller cross-sectional width than the cross-sectional width defined by the interior surface 114 of the sidewall 112. The reduced cross-sectional width defined by the longitudinal protrusion 120 prevents or reduces lateral movement of the ball valve 190 toward the sidewall 112, while providing a flow path for fluid to flow past the ball valve 190 when the seal between the distal wall 130 and the ball valve 190 is released.

In one or more embodiments, the cross-sectional width of the interior surface 114 of the chamber 116 and the cross-sectional width of the ball valve 190 are sized to permit movement of the ball valve 190 distally and proximally within the chamber 116 but prevent lateral movement of the ball valve 190 toward the sidewall 112 of the housing, which may occur when the flow rate of the medication is low and less pressure is being exerted on the ball valve 190 in the distal direction.

In one or more embodiments, a plurality of longitudinal protrusions 121 is provided along the length of the housing 110, as shown in FIGS. 7-8. The plurality of longitudinal protrusions 121 reduce the cross-sectional width of the chamber 116 within which the ball valve 190 may move in the proximal and distal direction but provide multiple flow paths for fluid to flow past the ball valve 190 when the seal between the perimeter 134 of the distal wall 130 and the ball valve 190 is released.

Figure 10:
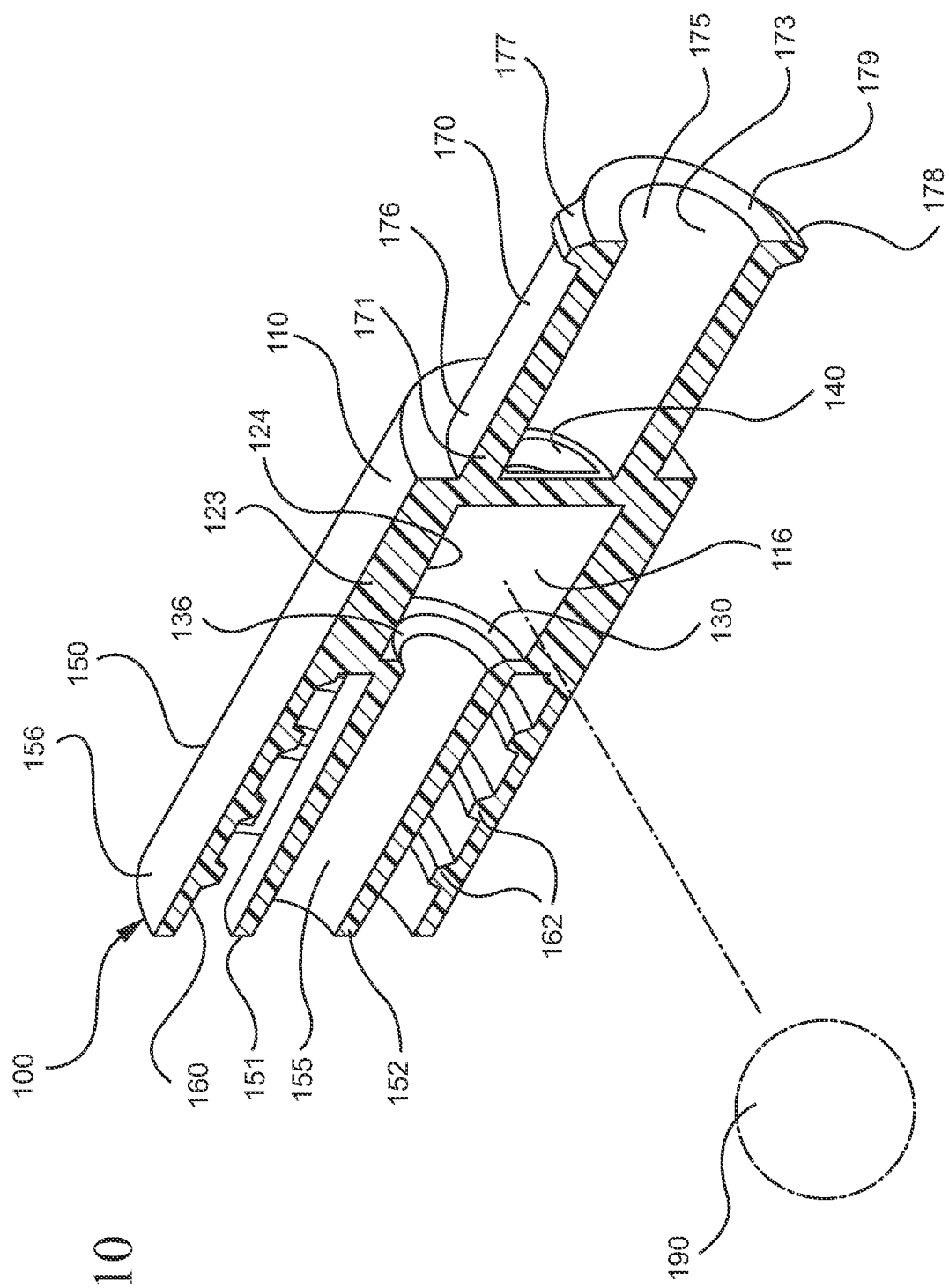
FIG. 10 shows a view of the drug delivery connector shown in FIG. 7 including a distal wall and sidewall according to one or more embodiments of the present invention and a ball valve.

The length, dimensions and/or placement of the longitudinal protrusions or other similar structure may be modified according to the needs of a particular application. For example, if the drug delivery connector is used with a medication that is more viscous, larger or more flow paths may be needed to facilitate flow between the container and the delivery site. In another example, in one or more embodiments, as shown in FIG. 10, the interior surface of chamber may include a plurality of ribs 122 extending from the distal wall 130 to a proximal wall 140 to align the ball valve 190 in the center of the fluid path without significantly reducing the flow rate of the medication flowing from a container through the drug delivery connector 100. As shown in FIG. 10, the plurality of ribs 122 provides additional fluid flow paths for the fluid, once the seal between the distal wall 130 and the ball valve 190 is released. The plurality of ribs 122 is configured to permit rotational and non-rotational movement of the ball valve 190 in the distal and proximal directions within the chamber. In a specific embodiment, the interior surface 114 of the chamber 116 includes two or more ribs (not shown) permit fluid communication between the distal connection portion 150 and the chamber 116 when the seal between the ball valve 190 and distal wall 130 is released.

Figure 11:
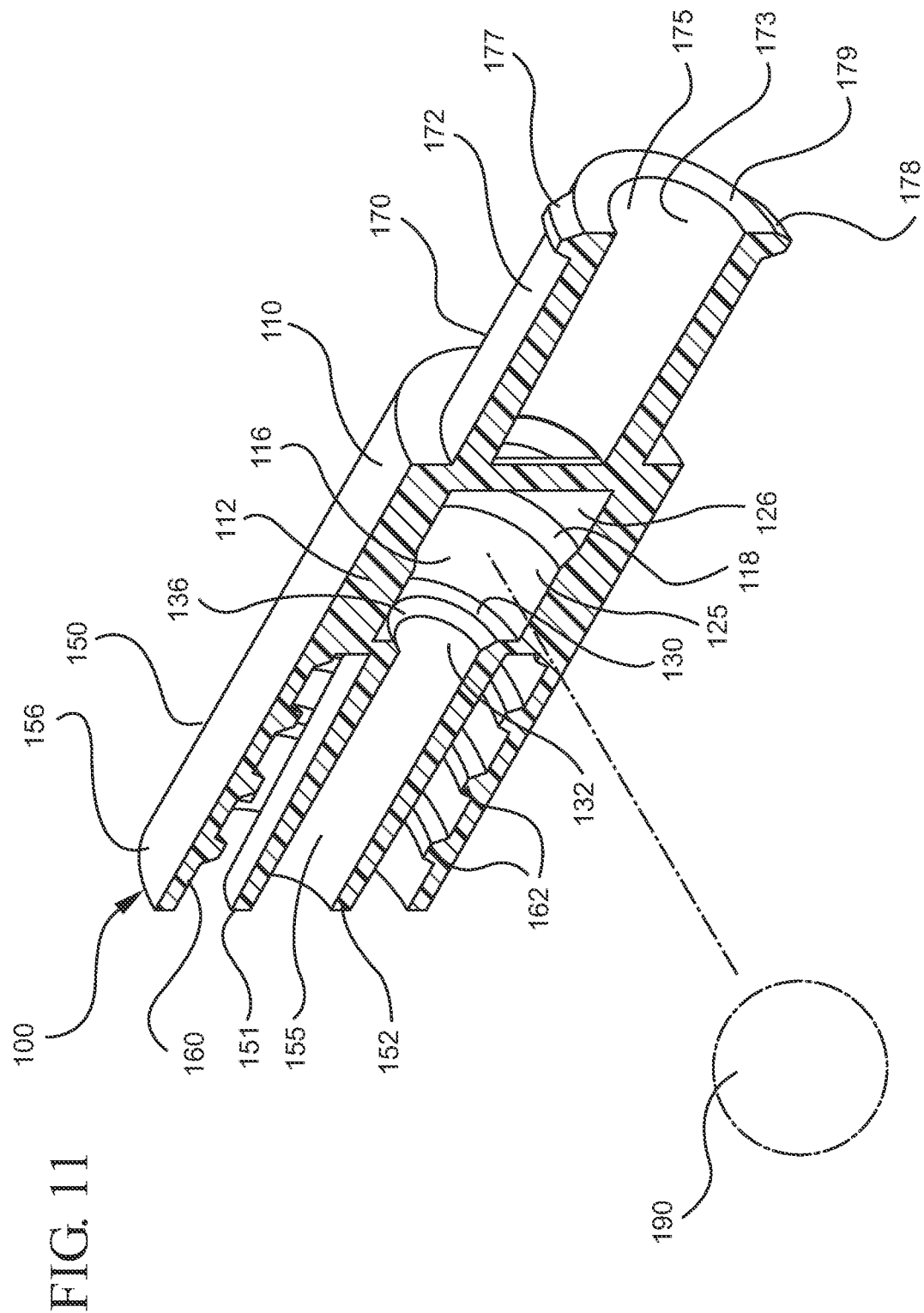
FIG. 11 shows a view of the drug delivery connector shown in FIG. 7 including a distal wall and sidewall according to one or more embodiments of the present invention and a ball valve.

In a specific embodiment, as shown in FIG. 11, the cross-sectional width of the interior surface 114 of the sidewall 112 may increase from the distal connection portion 150 to the proximal connection portion 170. In one or more embodiments, the cross-sectional width of the interior surface 114 of the sidewall 112 may increase linearly. In the embodiment shown in FIG. 10, the housing 110 includes an expanding sidewall 123 including an inside surface 124 defining a cross-sectional width that increases substantially linearly or constantly from the distal end 111 to the proximal end 119 of the housing. In the embodiment shown in FIG. 11, the cross-sectional width of the sidewall 112 increases "stepwise" along the axial length of the sidewall 112. In such embodiments, the sidewall 112 has a first portion 125 extending from the distal wall 130 along the axial length of the sidewall 112 for a first length and a second portion 126 extending from the first portion 125 to the proximal wall 140. The cross-sectional width of the first portion 125 may be smaller than the cross-sectional width of the second portion 126. In one or more embodiments, the cross-sectional width of the first portion 125 may increase from the distal wall 130 to the second portion 126 or remain constant. In one or more embodiments, the cross-sectional width of the second portion 126 may increase from the first portion 125 to the proximal wall 140 or may remain constant. In another embodiment, the cross-sectional width of the first portion 125 and the second portion 126 increases at the same or different rates. As shown in FIG. 11, a transition portion 118 may be included between the first portion 125 and the second portion 126. In the embodiment shown, the cross-sectional width of the first portion 125 is smaller than the second portion 126 but is constant from the distal wall 130 to the transition portion 118. The second portion 126 is shown as having a cross-sectional width larger than the first portion 125 but is constant from the transition portion 118 to the proximal wall 140 with the transition portion 118 having a cross-sectional width that increases from the first portion 125 to the second portion 126.

Figure 12:
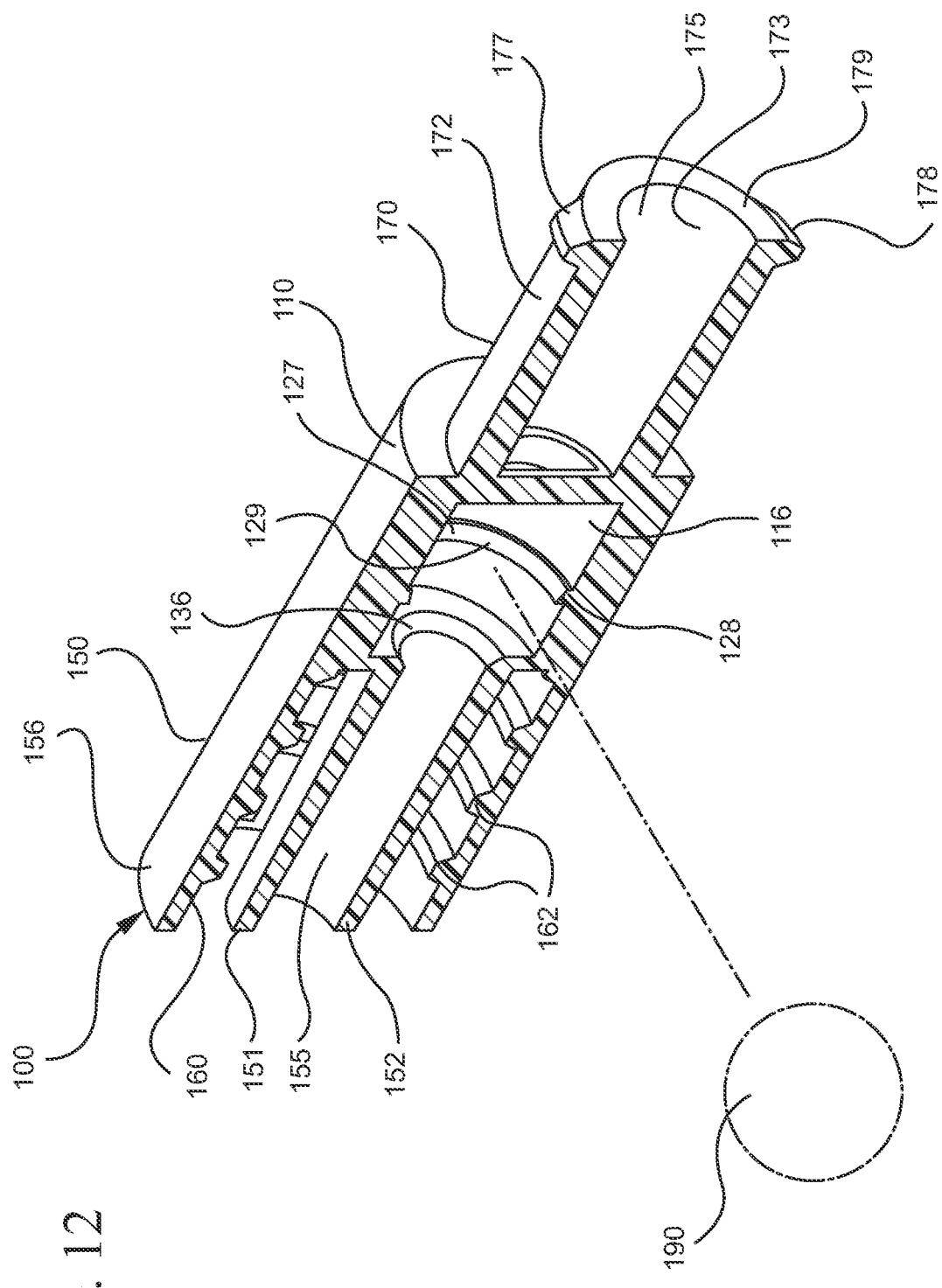
FIG. 12 shows a view of the drug delivery connector shown in FIG. 7 including a distal wall and sidewall according to one or more embodiments of the present invention and a ball valve.

In one or more embodiments, the sidewall 112 of the chamber 116 may include one or more structural features to align the ball valve in the center of the fluid path. These structural features may also exert a distally directed force on the ball valve 190 to prevent the ball valve 190 from moving in the proximal direction, when the force exerted on the ball valve varies, for example, during air priming or the removal of air from within the syringe or container and before delivery of the medication to the intended delivery site. In one or more embodiments, these structural features prevent movement of the ball valve 190 in the proximal direction and require the exertion of a greater force on the ball valve 190 to move the ball valve 190 in the proximal direction. In one or more embodiments, a structural feature that prevents movement of the ball valve 190 in the proximal direction is shown in FIG. 12. In FIG. 12, the sidewall 112 of the housing 110 the sidewall defines a radial length or circumference and includes a retainer ring 127 extending radially inwardly into the chamber 116. The retaining ring 127 may be formed along discrete portions of the radial length of the sidewall 112 or, alternatively, along the entire radial length of the sidewall 112. In one or more embodiments, the retaining ring 127 includes a perpendicular wall 128 extending radially inwardly into the chamber 116 from the sidewall 112 that defines a cross-sectional width along the retaining ring 127 that is smaller than the cross-sectional width of the sidewall 112. In one or more embodiments, the perpendicular wall 128 includes a beveled inside edge 129. In such embodiments, the beveled inside edge 129 may define a cross-sectional width at increases in the proximal direction along the axial length of the perpendicular wall 128. In an alternative embodiment, the beveled inside edge 129 may define a cross-sectional width that decreases in the proximal direction. In one or more embodiments, the beveled inside edge 129 retains the ball valve 190 in the closed position in contact with the perimeter 134 of the distal wall 130 by forming a physical barrier to movement of the ball valve 190 in the proximal direction. In one or more embodiments, the perpendicular wall may include a flat inside edge (not shown) that defines a constant cross-sectional width along the axial length of the perpendicular wall 128.

In an even more specific embodiment, the interior surface 114 of the chamber 116 and/or the retaining ring 127 may include one or more raised portions (not shown) extending radially that also form a physical barrier to movement of the ball valve 190 in the proximal direction but also provide an open flow path for medication to flow from a syringe barrel through the drug delivery connector 100 when the drug delivery connector 100 is attached to a actuator and the seal between the ball valve 190 and the perimeter 134 of the distal wall 130 is released. In one or more embodiments, the height of the raised portions (not shown) may be adjusted to exert more or less pressure on the ball valve in the distal direction. For example, the height and/or shapes of the raised portions may be increased to exert a greater force on the ball valve in the distal direction and/or to form a physical barrier that is more difficult to overcome than raised portions having a decreased height. In one or more embodiments, the raised portions may also be beveled to exert an even greater force on the ball valve in the distal direction to prevent proximal movement thereof. The chamber of one or more embodiments may include a combination of the longitudinal protrusion 120, the plurality of longitudinal protrusions 121, expanding sidewall 123, the retaining ring 127 and/or the plurality of raised portions (not shown).

Figure 13:
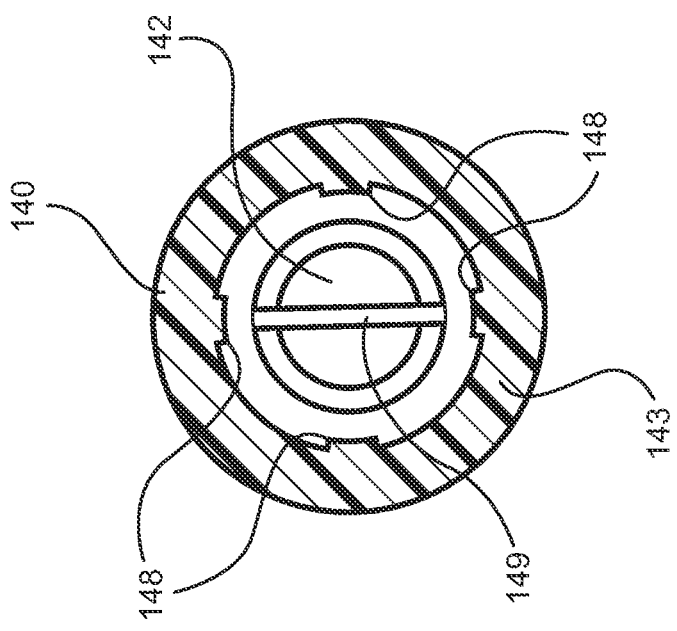
FIG. 13 illustrates a cross-sectional view of the proximal end of the drug delivery connector shown in FIG. 4 taken along line 13-13 including a proximal wall according to one or more embodiments of the present invention.

The aperture 142 of the proximal wall 140 of the housing 110 provides fluid communication between with the chamber 116 and the open proximal end 179 of the proximal connection portion 170. In one or more embodiments, the proximal wall 140 may include more than one aperture 142. As shown in FIGS. 13-15, the proximal wall 140 may also include a structure to prevent the formation of a seal between the ball valve 190 and the aperture 142. In other words, the proximal wall 140 includes a structure that maintains fluid communication between the chamber 116 and the proximal connection portion 170. In one or more embodiments, the proximal wall 140 may include an irregular contour or geometry that prevents the formation of a seal between the ball valve 190 having a regular spherical geometry.

In one or more embodiments, the proximal wall 140 may include a series of telescoping conduits extending in a fixed position with respect to each other and extend from the chamber 116 to the proximal connection portion 170. FIGS. 13-15 illustrate embodiments which utilizes telescoping conduits that surround the aperture 142 and defining a conduit space. In such embodiments, a first conduit 143 extends in the proximal direction from the side wall 112 of the housing 110 and defines a first cross-sectional width, a second conduit 144 defining a second cross-sectional width extends from the first conduit 143 in the proximal direction to a third conduit 145 defining a third cross-sectional width extends from the second conduit 144 in the proximal direction. In one or more embodiments, the telescoping conduits have varying axial lengths extending in the proximal direction. The cross-sectional widths defined by the telescoping conduits may further decrease from the first conduit 143 to the third conduit 145 further have a decreasing cross-sectional width. For example, the first cross-sectional width of the first conduit 143 may be larger than the second cross-sectional width of the second conduit 144. In one or more embodiments, the second cross-sectional width of the second conduit 144 may be larger than the third cross-sectional width of the third conduit 145.

Figure 13A:
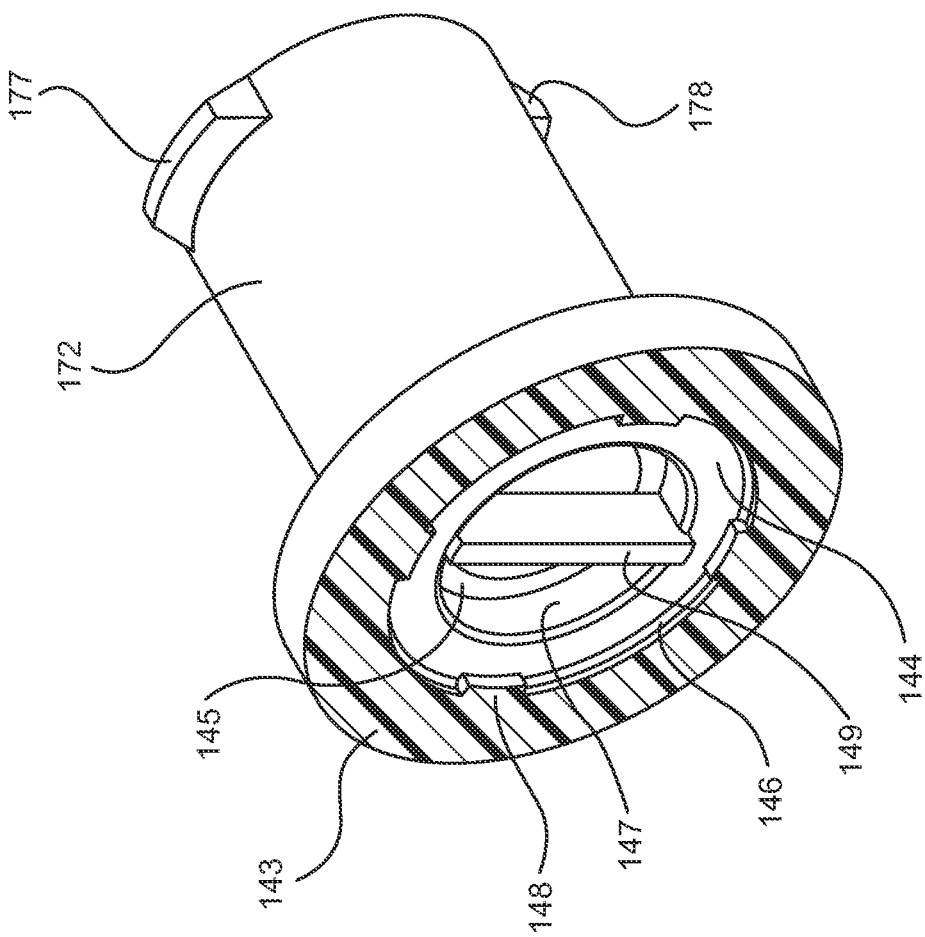
FIG. 13A shows a perspective view of the drug delivery connector shown in FIG. 13.

In one or more embodiments, the first conduit 143 may include first inside surface 146 defining a first conduit space in fluid communication with the aperture 142. The first inside surface includes one or more guide bars 148 extending partially into the first conduit space. In one or more embodiments, the one or more guide bars 148 extend along the axial length of the first conduit 143 and are disposed at equal distances along the first inside surface 146. In one or more embodiments, the second conduit 144 may include a second inside surface 147 defining a second conduit space and includes at least one transverse beam 149 extending across the aperture 142, intersecting the aperture 142 into two openings along the axial length of the second conduit 144. In the embodiment shown in FIGS. 14 and 14A, the second conduit 144 includes two transverse beams 149 extending from equally spaced points along the second inside surface 147 of the second conduit 144 and intersecting at a midpoint in the aperture 142, intersecting the aperture 142 into four equally sized openings along the axial length of the second conduit 144. In the embodiment shown in FIGS. 15 and 15A, the second conduit 144 includes three transverse beams 149 extending from equally spaced points along the second inside surface 147 toward a mid-point in the aperture 142. The three transverse beams 149 shown in FIGS. 15 and 15A intersect the aperture 142 into three equally sized openings along the axial length of the second conduit 144. In one or more embodiments, the transverse beam or beams 149 have an axial length that extends along the axial length of the second conduit 144 and occupies the second conduit space. In a more specific embodiment, the transverse beam or beams 149 may have an axial length that extends beyond the axial length of the second conduit 144 and extends into the first conduit space of the first conduit 143. FIGS. 13A, 14A and 15A illustrate one or more transverse beams 149 that extend into the first conduit space. In one or more embodiments, the third conduit 145 is free of any additional structures and surrounds the aperture 142 adjacent to the proximal connection portion 170.

The arrangement of the guide bars 148, the first conduit 143, second conduit 144, third conduit 145 and/or transverse beam 149 prevent formation of a seal between the ball valve 190 and the proximal wall 140 because they do not provide a circular edge with which the ball valve 190 may from a line contact interaction. Instead, the guide bars 148, the first conduit 143, second conduit 144, third conduit 145 and/or transverse beam 149, alone or in combination, form an irregular edge or irregular contact points with the ball valve 190 that prevent the formation of a seal between the ball valve 190 and the proximal wall 140.

In one more alternative embodiments, the proximal wall 140 may include a plurality of telescoping walls (not shown) extending proximally in a fixed configuration and surrounding the aperture 142 for preventing the formation of a seal between the ball valve and the proximal wall. The plurality of telescoping walls including a first annular wall (not shown) disposed adjacent to the sidewall of the housing, a second annular wall (not shown) between the first annular wall and a third annular wall (not shown). In one or more embodiments, the third annular wall (not shown) is disposed between the second annular wall (not shown) and the aperture 142. The first annular wall (not shown), second annular wall (not shown) and/or third annular wall (not shown) may have a thickness that elongates the chamber 116 and extends the chamber 116 at least partially into the interior 175 of the proximal connection portion 170. The first annular wall (not shown) may have a first thickness and the second annular wall may have a second thickness, wherein the first and second thicknesses may be the same or different. The third annular wall (not shown) may be integrally formed with the proximal connection portion 170 and may define the aperture 142.

In one or more embodiments, the first annular wall (not shown) may include a plurality of detents (not shown) that extend inwardly onto the second annular wall (not shown). The plurality of detents (not shown) are shaped and disposed to prevent formation of a seal between the ball valve 190 and the proximal wall 140. In one or more embodiments, the plurality of detents (not shown) may be disposed on the second annular wall (not shown) and extend inwardly onto the third annular wall (not shown). The plurality of detents (not shown) may be disposed equidistant from the aperture 142 and each other along the perimeter of the one or more of the first annular wall (not shown), second annular wall (not shown), and/or third annular wall (not shown). In one or more specific embodiments, four detents may be utilized and may be disposed along the first annular wall (not shown) so that they extend inwardly and onto the second annular wall (not shown).

In one or more embodiments, one or more of the first annular wall (not shown), second annular wall (not shown) and/or third annular wall (not shown) may include at least one transverse beam extending across the aperture from opposite ends of the wall. In a specific embodiment, the second annular wall may include a single transverse beam attached at opposite sides of the second annular wall (not shown) and extending across the aperture 142. The second annular wall may also include two transverse beams (not shown) that intersect at the mid-point of the aperture 142 and divide the at least one aperture 142 into four apertures. In a more specific embodiment, the second annular wall may include three transverse beams (not shown) extending into the aperture 142 and intersecting at a mid-point of the aperture 142. In such embodiments, the three transverse beams (not shown) divide the at least one aperture 142 into three apertures. The transverse beam (not shown) may be raised from the annular wall on which it is formed and/or connected so it extends proximally into the chamber. In other words, the transverse beam (not shown) may extend proximally from the first annular wall (not shown), second annular wall (not shown) and/or third annular wall (not shown) into the chamber 116 to create provide an unlevel surface or seat for the ball valve 190 adjacent to the first, second and/or third annular walls.

The arrangement of the detents (not shown), the first annular wall (not shown), second annular wall (not shown), third annular wall (not shown) and/or transverse beam (not shown), described herein, prevent formation of a seal between the ball valve 190 and the proximal wall 140 because they do not provide a circular edge with which the ball valve 190 may from a line contact interaction. Instead, the detents (not shown), the first annular wall (not shown), second annular wall (not shown), third annular wall (not shown) and transverse beam (not shown) form an irregular edge or irregular contact points with the ball valve 190, which together and individually, prevent the formation of a seal between the ball valve 190 and the proximal wall 140.

Figure 16:
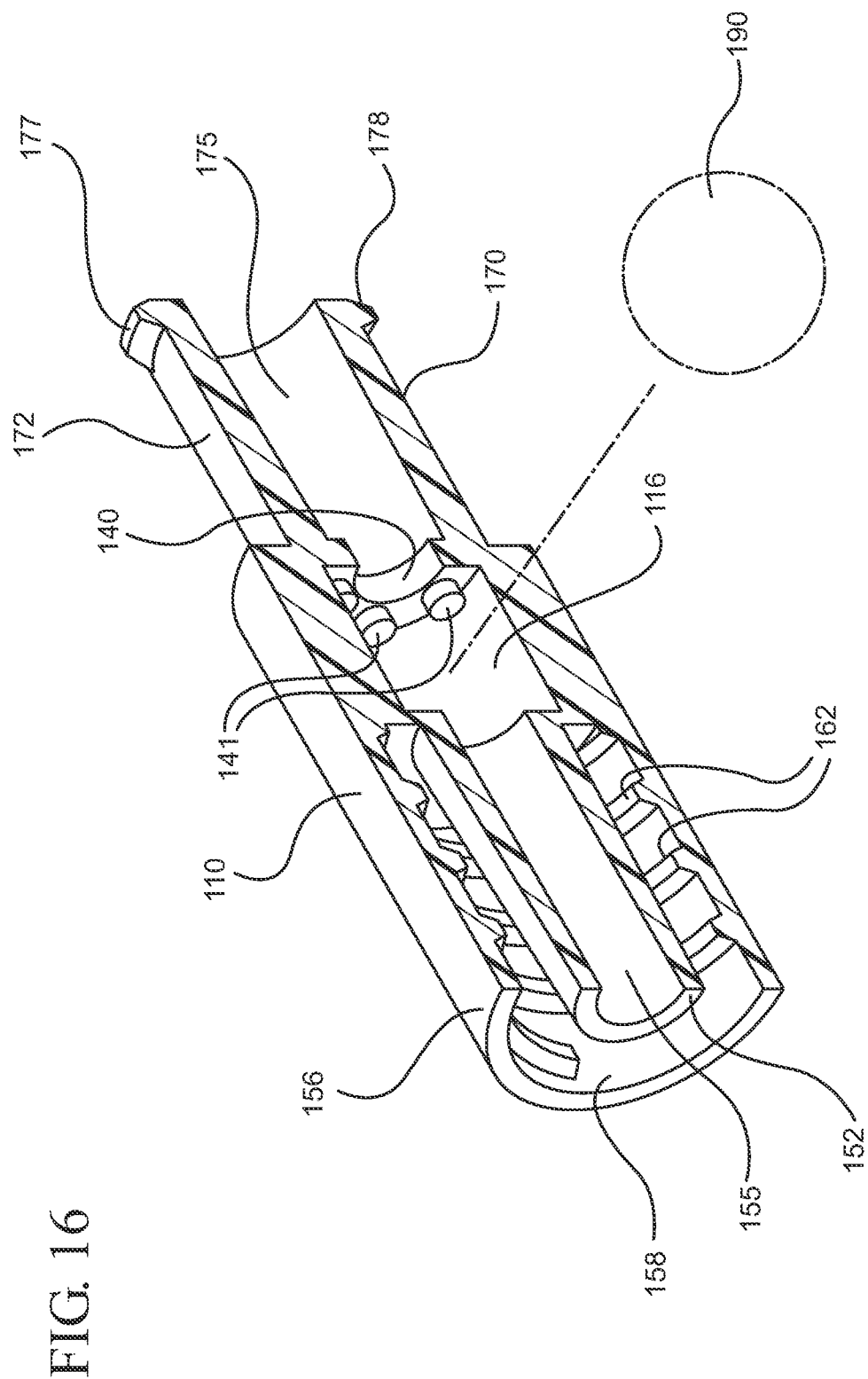
FIG. 16 shows a perspective cross-sectional view of a drug delivery connector according to one or more embodiments.

In alternative embodiments, the proximal wall 140 may utilize other means to prevent formation of a seal between the ball valve 190 and the at least one aperture 142. For example, the proximal wall 140 may include a plurality of apertures (not shown) dispersed along the proximal wall 140. In this embodiment, the at least one aperture 142 disposed along the proximal wall 140 remain open regardless of the position of the ball valve 190. In one or more embodiments, as shown in FIG. 16, the proximal wall 140 may include one or more protuberances 141 extending distally into the chamber 116 that prevent the ball valve 190 from being forming a seal with the proximal wall 140.

An actuator 200 may be provided with the drug delivery connector 100 either separately or pre-attached to a catheter connector 210. A syringe barrel 300 and/or a hypodermic needle 400, which may include a metal or plastic cannula that may be blunt, may also be provided separately or attached to the drug delivery connector 100. The hypodermic needle 400 may be provided with a needle hub 410, as shown in FIG. 17. In one or more embodiments, the drug delivery connector 100, syringe barrel 300 and hypodermic needle 400 are provided in a kit. In a specific embodiment, the drug delivery connector 100, syringe barrel 300, hypodermic needle 400 and actuator 200 may be provided in a kit. In a more specific embodiment, the drug delivery connector 100, syringe barrel 300, hypodermic needle 400, actuator 200 and catheter connector 210 may be provided in a kit. In one or more embodiments, the catheter connector 210 may optionally include a filter. Alternatively, the drug delivery connector 100, syringe barrel 300, actuator 200, catheter connector 210, hypodermic needle 400 and/or filter may be provided separately.

In one or more alternative embodiments, the drug delivery connector is connected to a syringe barrel. The drug delivery connector can be pre-attached to the syringe by the device manufacturer. The syringe barrel may be pre-filled or may be filled by the user using a standard plunger rod and/or a hypodermic needle, or other means. A typical syringe barrel that may be utilized with one or more drug delivery connectors 100 is shown in FIG. 1 and includes a distal end 321 and an open proximal end 329 and an end wall 322. A sidewall 324 may extend from the distal end 321 to the open proximal end 329 and may include an interior surface 326 that defines a chamber 328 for holding liquids. The distal end 321 of the syringe barrel 300 may also include an open tip in fluid communication with the chamber 328.

A needle cannula (not shown) having a lumen (not shown) may be attached to the open tip 314 of the syringe barrel for aspirating or filling the syringe barrel 300 with medication. When attached to the open tip 314, the lumen (not shown) is in fluid communication with the open tip 314 and the chamber 328 of the syringe barrel. The syringe barrel 300 may include a luer lock attachment 310 or may also include or a luer slip fitting (not shown). The proximal connection portion 170 of embodiments of the drug delivery connectors 100 described herein may include either corresponding fitting for secure engagement of syringe barrels having both types of luer fittings.

In one or more embodiments, permanent connection mechanisms may be built in the drug delivery connector 100, so that, upon connection of drug delivery connector 100 on to the syringe barrel 300 or other container the connection becomes permanent and the drug delivery connector and syringe barrel 300 or other container are not detachable. Permanent connection mechanisms may also be built in the actuator 200 so that, upon connection of actuator 200 to the catheter connector 210 or other drug delivery site, which may include a filter, the connection the connection becomes permanent and the actuator 200 and the catheter connector 210 are not detachable. The purpose of the permanent connection is to prevent disconnections between the drug delivery connectors and containers or actuator and catheter connectors or other drug delivery sites, leaving only the joint between the drug delivery connector 100 and the actuator 200 being detachable. The permanent connection can be realized by welding, which may include ultrasonic welding, gluing, or through design, for example, by incorporating one or more ratchet connector, special threads and other structures known in the art.

Alternatively, instead of pre-assembling, the drug delivery connector 100, actuator 200, syringe barrel 300 and/or catheter connector 210 may be packed in the procedure trays or provided as standalone units. In such embodiments, the permanent connections can be built into one or more of the drug delivery connector 100 and/or actuator 200 by incorporating ratchet connections, threaded connections or other known structures for connection known in the art.

In one or more embodiments the drug delivery connector 100 may be attached to the syringe barrel 300 when it is empty. Upon connection of the drug delivery connector 100 and the syringe barrel 300, the ball valve 190 forms a seal with the distal wall 130 of the drug delivery connector 100 once medication enters the chamber 116 of the drug delivery connector. In embodiments which incorporate a spring loaded ball valve 190, the ball valve 190 forms a seal with the distal wall 130 of the drug delivery connector 100 whether or not medication enters the chamber 116 of the drug delivery connector. In one or more embodiments, the presence of air within the syringe barrel 300 does not necessarily close the ball valve 190 and permits the user to expel any air from within the syringe barrel 300. The formation of the seal between the ball valve 190 and the distal wall 130 prevents the air and/or medication contained within the syringe barrel 300 from exiting through the bore 132 of the distal wall 130. The drug delivery connector 100 may remain unconnected or attached to an actuator 200, until the point at which the medication contained within the syringe barrel 300 is ready to be delivered or administered to a patient.

To fill the syringe barrel 300, a hypodermic needle 400 may be attached to the distal end of the drug delivery connector 100 that is attached to a syringe barrel 300. As shown in FIG. 17, the hypodermic needle 400 is attached to the distal connection portion 150 of the drug delivery connector 100 using a needle hub 410. In one or more embodiments, needle hub 410 may include an open distal end 411, an open proximal end 419 and a hub body 412 extending from the open distal end 411 to the open proximal end 419. The hypodermic needle 400 may be attached to the open distal end 411 using methods known in the art, including adhesive and the like. The hub body 412 includes an inside surface 414 defining a hub cavity 416.

In one or more embodiments, the hub body 412 includes an outside surface 418. The outside surface 418 may include a projection 417 or ridge disposed adjacent to the open proximal end 419 and extending outwardly from the outside surface 418 for engagement with the distal connection portion 150. In one or more embodiments, the projection 417 has a shape and/or dimension to engage the treaded portion 162 disposed on the inside surface 158 of the coaxial wall 156 of the distal connection portion 150.

In one or more embodiments, the outside surface 154 of the elongate tube 152 is tapered or has a cross-sectional width that increases from the sidewall 112 of the housing to the open distal end 101 of the housing. In one or more alternative embodiments, outside surface 154 of the elongate tube 152 is contoured or is shaped to frictionally engage the inside surface 414 of the hub 440. According to a specific embodiment, the inside surface 414 of the hub body 412 is contoured or shaped to frictionally engage the outside surface 154 of the elongate tube 152 of the distal connection portion 150.

After attachment of the hypodermic needle 400 to the distal connection portion 150 of the drug delivery connector, the desired amount of medication can be aspirated or filled into the syringe barrel 300. In the embodiment shown in FIG. 17, the syringe barrel 300, drug delivery connector 100 and hypodermic needle 400 are positioned to draw medication from a medication source, shown in FIG. 16 as a vial 420. A plunger rod 320 is shown inserted into the syringe barrel 300 and a force is applied to the plunger rod in the proximal direction drawing medication into the syringe barrel 300.

Figure 19:
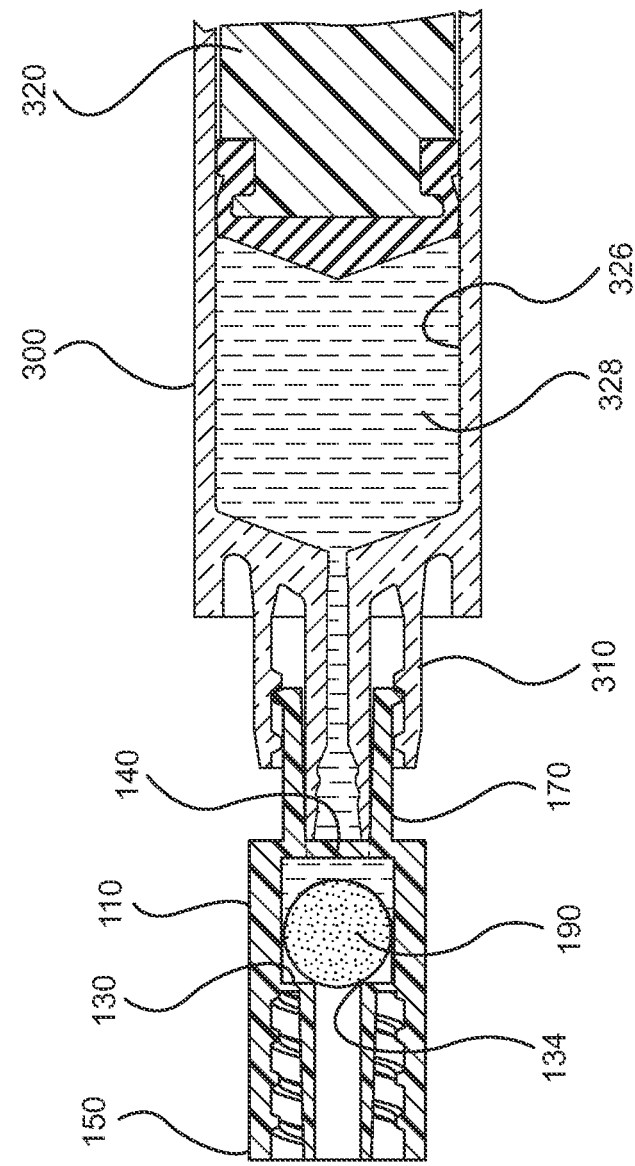
FIG. 19 illustrates a cross-sectional view of the drug delivery connector and syringe barrel shown in FIG. 18 filed with liquid.

As shown in FIG. 18, the force of the medication being drawn or aspirated into the syringe barrel 300 applies a force on the ball valve 190 in the proximal direction, releasing the seal between the ball valve 190 and the distal wall 130 of the drug delivery connector 100. The medication enters the chamber 116 of the drug delivery connector 100 and passes through the proximal connection portion 170 into the syringe barrel. After drawing the desired amount of medication, the hypodermic needle may be removed. Once the hypodermic needle is removed, as shown in FIG. 19, the ball valve 190 closes and forms a fluid-tight seal with the distal wall 130 of the drug delivery connector 100. Specifically, the medication within the syringe barrel 300 exerts a force on the ball valve in the distal direction, forcing the ball valve against the distal wall 130, or more particularly, the perimeter 134 of the distal wall 130. When a bolus is needed, the syringe barrel-drug deliver connector assembly is connected to an actuator 200.

In one or more embodiments, when the drug delivery connector 100 and a container, for example the syringe barrel 300, are attached, the user may remove air from the syringe barrel 300 by inverting the syringe barrel 300 and drug delivery connector 100 or position the assembled syringe barrel 300 and drug delivery connector 100 so the medication within the syringe barrel 300 moves, by gravity, in the proximal direction relative to the drug delivery connector 100 and the air within the syringe barrel 300 moves, by gravity, in the distal direction relative to the medication into the chamber 116 of the drug delivery connector 100. In this position, the ball valve 190 will float or drop down toward the proximal wall 140 and the seal between the ball valve 190 and the distal wall 130 is released. As the user applies a force to the plunger rod 320 of the syringe in the distal direction, the air trapped within the chamber 116 of the drug delivery connector 100 and/or syringe barrel 300 is allowed to escape through the aperture 142 of the proximal wall 140 and the open distal end 151 of the distal connection portion 150. Simultaneously, the medication contained within the syringe barrel 300 is forced into the chamber 116 of the drug delivery connector 100 by the force exerted on the medication by the plunger rod 320. The medication entering the chamber 116 exerts a force or pressure on the ball valve 190 in the distal direction, causing the ball valve 190 to move distally and reform the seal with the distal wall 130 and prevent fluid communication through the bore 132 of distal wall 130. The sealed bore 132 prevents the user from directly injecting the medication contained within the syringe barrel 300 into any port without the use of an actuator having a specific shape and/or dimensions to open the seal.

To open the ball valve 190 and administer the medication contained within the syringe barrel 300, the actuator 200 is attached to the open distal end 101 of the drug delivery connector 100. The actuator 200 includes a catheter connector 210. As shown in more detail in FIGS. 20-21, suitable actuators 200 include an open distal end 211, a proximal end 219, and a longitudinally extending projection 212 extending in the proximal direction from the distal end 211 to the proximal end 219. The proximal end 219 of the actuator 200 is unattached to any structure and may be described as "cantilevered" or a projection 212 that is supported on only one end. The proximal end 219 of the actuator 200 may be described as a blunt tip or rounded tip. In one or more embodiments, the proximal end 219 has an outer diameter that is larger than the inner diameter of standard luer slip connections utilized in most IV medication delivery syringes to prevent accidental connection of IV medication-containing syringes with the actuator 200 and to prevent access to the anesthesia catheter.

In one or more embodiments, the projection 212 has a length that permits the proximal end 219 of the actuator 200 to extend into the chamber 116 of the drug delivery connector 100, upon attachment of the actuator 200 to the distal connection portion 150 of the drug delivery connector 100. The projection 212 includes one or more apertures or open paths 214 extending along the length of the projection 212 to permit the medication within the syringe barrel 300 and chamber 116 of the drug delivery connector 100 to flow from the drug delivery connector 100 to a delivery site that is attached to the distal end 211 of the actuator 200. In one or more embodiments, the projection 212 is in the form of two perpendicularly intersecting beams that extend in the proximal direction and define four openings. In one or more embodiments, the intersecting beams may include a solid end at the proximal end 219 of the actuator 200. In one or more embodiments, the solid end is in the form of a hemi-sphere (not shown). In a specific embodiment, the projection 212 is in the form of a single, proximally extending beam (not shown) that defines two apertures or open paths 214. In a more specific embodiment, the projection 212 includes a hollow member (not shown) that extends proximally and includes a conduit (not shown) extending from the open distal end 211 to the apertures or open paths 214 at the proximal end 219 of the actuator 200.

Figure 20:
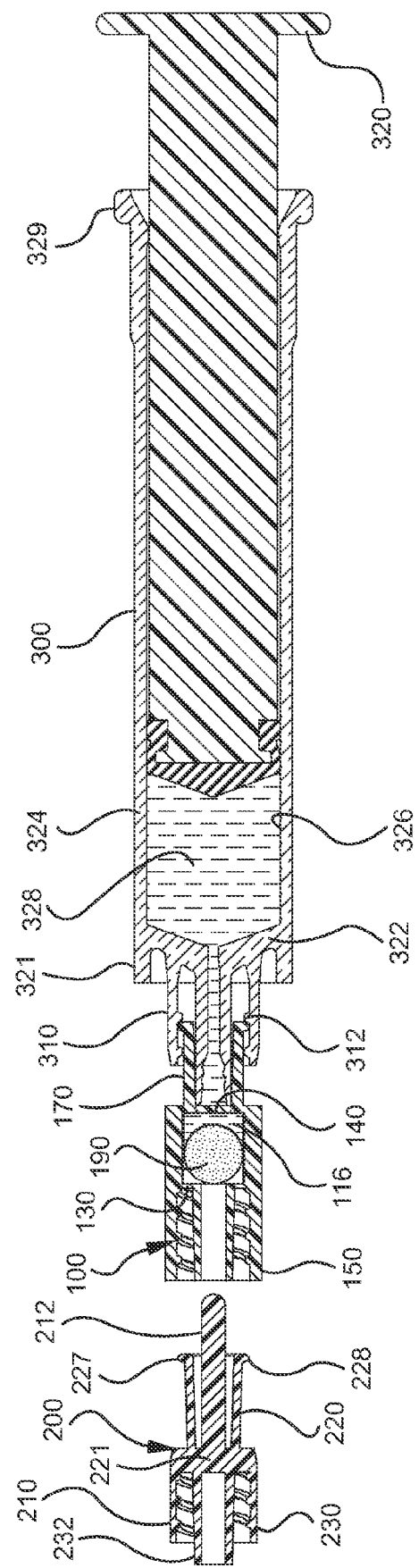
FIG. 20 shows a cross-sectional view of the drug delivery connector shown in FIG. 5 assembled with a syringe and an unassembled actuator according to one or more embodiments.
Figure 21:
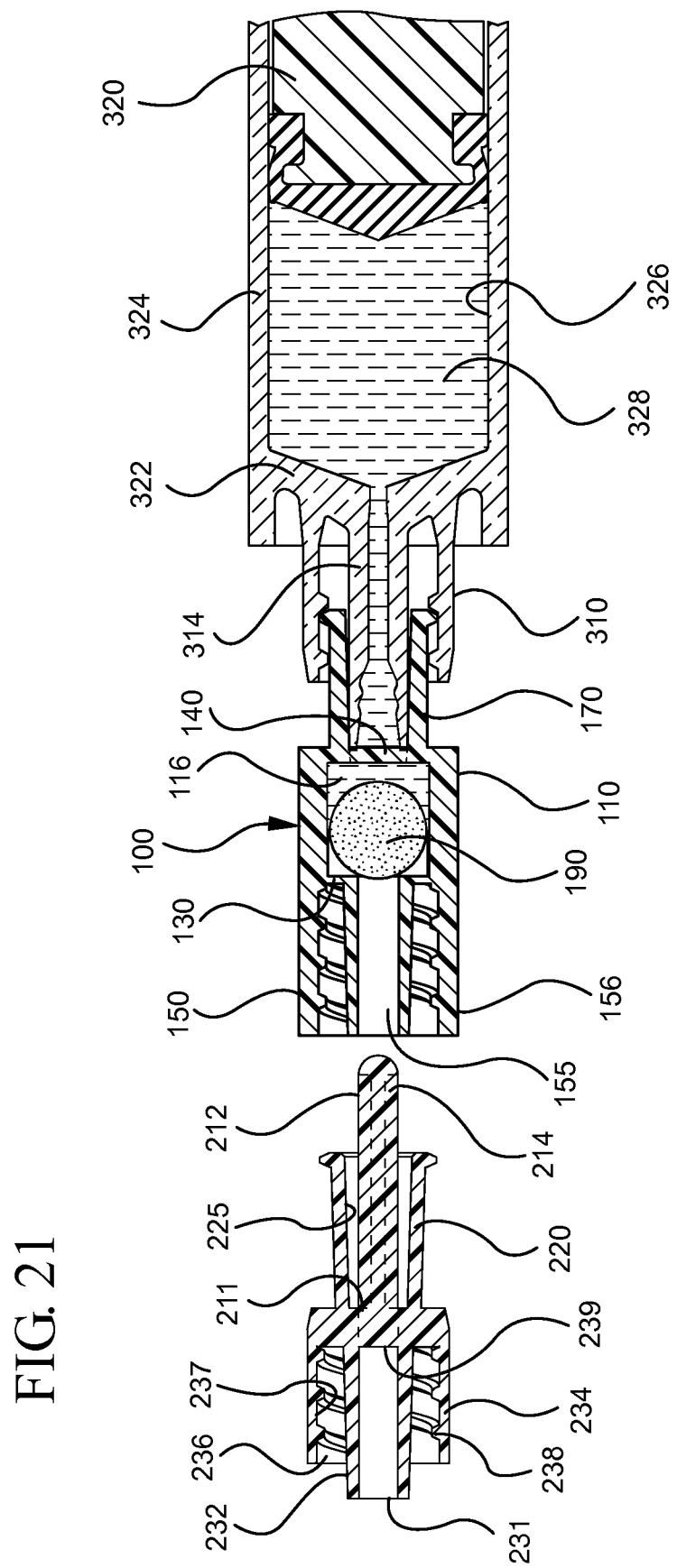
FIG. 21 shows an enlarged partial view of the drug delivery connector, syringe and actuator shown in FIG. 20.

In the embodiment shown in FIGS. 20-21, the actuator includes a female fitting or a hub 220. In one or more embodiments, the hub 220 includes an open proximal end 229, an open distal end 221 and a wall 222 extending from the open proximal end 229 to the open distal end 221 of the hub. The open distal end 211 of the projection 212 is attached to the open distal end of the hub 220 and extends along the length of the hub 220 to the open proximal end 229. In one or more embodiments, the wall 222 includes having an outside surface 224 that includes a luer lock structure. In a specific embodiment, the luer lock structure includes at least one radially outwardly extending portion that engages the threaded portion 162 disposed on the inside surface 158 of the coaxial wall 156 of the distal connection portion 150 of the drug delivery connector. In the embodiment shown in FIGS. 1-23, the radially outwardly extending portion includes two radially outwardly extending tabs 227, 228. In an even more specific embodiment, the radially outwardly extending portion 226 includes a peripheral lip (not shown). In one or more embodiments, the inside surface 225 of the wall 222 may have a luer slip structure. In a specific embodiment utilizing a luer slip structure (not shown), the inside surface 225 of the wall may define a tapered cross-sectional width that increases from the open distal end 221 to the open proximal end 229 and is shaped or contoured to frictionally engage a standard luer slip male fitting incorporated in alternative embodiments of a distal connection portion 150.

In the embodiment shown, the wall 222 of the hub 220 is formed in a coaxial relationship to the projection 212 of the actuator and defines a cavity 216. The hub may be securely engaged to the distal end 211 of the drug delivery connector 100 by inserting the actuator 200 into the passageway 155 of the elongate tube 152 of the distal connection portion 150 of the drug delivery connector. Where the hub 220 utilizes a luer lock structure, the drug delivery connector 100 and/or the hub 220 may be rotated with respect to each other. In embodiments of the hub 220 utilizing a luer slip structure (not shown), the drug delivery connector 100 is inserted into the 216 cavity of the hub 220 until sufficient frictional interference is formed between the drug delivery connector 100 and the inside surface 225 of the hub 220.

Figure 22:
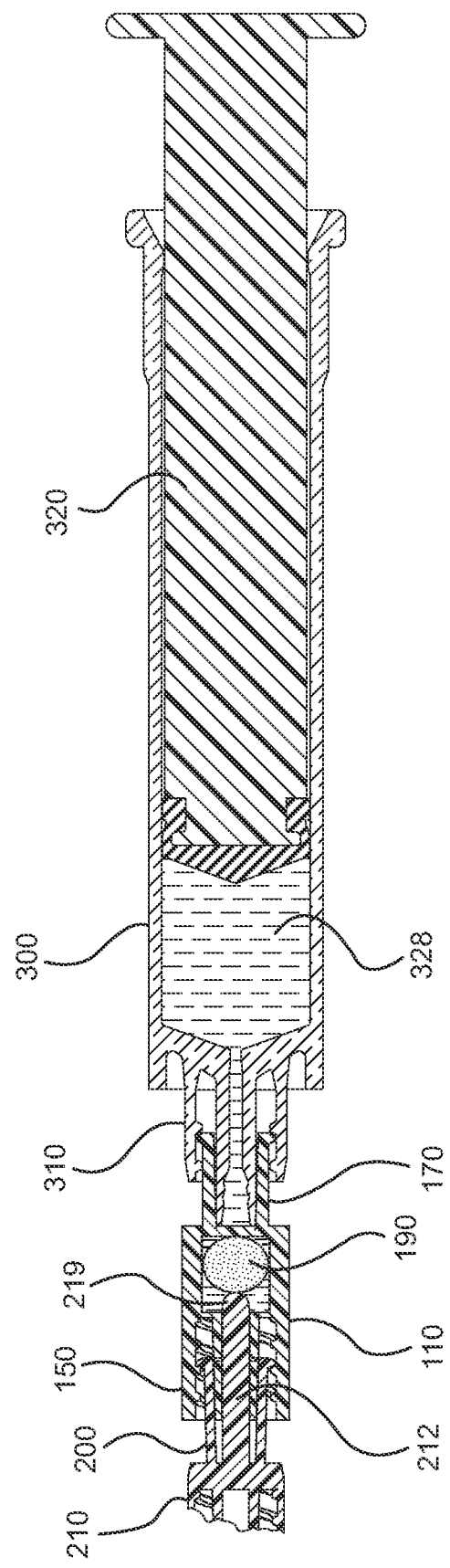
FIG. 22 illustrates the drug delivery connector and syringe and actuator of FIG. 20 in an assembled state.
Figure 23:
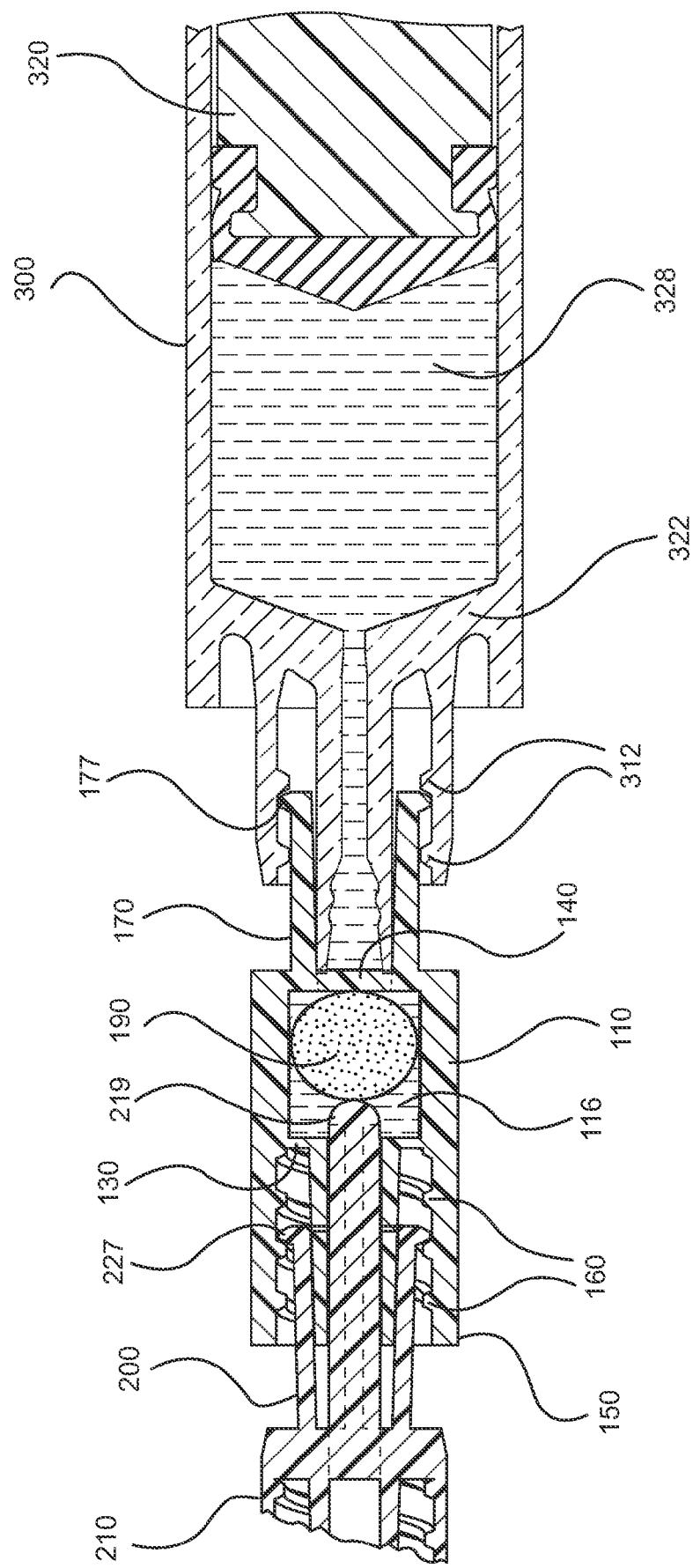
FIG. 23 illustrates an enlarged partial view of the drug delivery connector, syringe and actuator shown in FIG. 22.

In the embodiment shown in FIGS. 20-21, the projection 212 has an axial length that permits the proximal end 219 of the actuator 200 to exert a force on the ball valve 190 in the proximal direction and cause the ball valve 190 move in the proximal direction and release the seal between the ball valve 190 and distal wall 130, as shown in FIGS. 22-23. In one or more embodiments, the force exerted on the ball valve 190 in the proximal direction is greater than the force exerted on the ball valve 190 in the distal direction by the medication within the syringe barrel 300 and/or chamber 116 of the drug delivery connector 100. In an alternative embodiment of the drug delivery connector 100 which incorporates structure to prevent proximal movement of the ball valve 190, the force exerted on the ball valve 190 by the actuator 200 is greater than the force exerted on the ball valve 190 by the structures.

The amount of force exerted on the ball valve 190 may be adjusted to control or meter the flow rate of the medication through the projection 212. In one or more embodiments, the projection 212 causes movement of the ball valve in the proximal direction prior to full attachment of the hub 220 and the distal connection portion 150. In a specific embodiment, the projection 212 causes proximal movement of the ball valve 190 when the hub 220 is fully attached to the distal connection portion 150.

In accordance with one or more embodiments, the length of the projection 212 may be adjusted to control or meter the amount of force exerted on the ball valve 190 to control or meter the flow rate of the medication contained within the syringe barrel 300 and/or chamber 116 of the drug delivery connector 100. In a specific embodiment, the length of the distal connection portion 150 and/or hub 220 may be adjusted to control or meter the amount of force exerted on the ball valve 190 to control or meter the flow rate of the medication contained within the syringe barrel 300 and/or chamber 116 of the drug delivery connector 100. In such embodiments, the user may control the flow rate by the amount and direction of rotational force used to engaging the hub 220 and/or distal connection portion 150. For example, if the flow rate is to be increased, the user would rotate the hub 220 and/or distal connection portion 150 so the hub 220 moves in the proximal direction relative to the distal connection portion 150 and engages more of the threaded portion 162 or so the hub 220 and/or distal connection portion 150 are more fully or completely engaged. This relative proximal movement or increased level of engagement between the hub 220 and the distal connection portion 150 causes the projection 212 to apply a greater force in the proximal direction to the ball valve 190 and widening the space between the distal wall 130 and the ball valve 190. During this adjustment, the force applied by the projection 212 on the ball valve 190 would increase relative to the fluid pressure exerted on the ball valve 190 in the distal direction from the flow of the medication out of the syringe barrel 300. If the flow rate is to be decreased, the user would rotate the hub 220 and/or distal connection portion 150 to rotate the hub 220 and/or distal connection portion 150 so the hub 220 moves in the distal direction relative to the distal connection portion 150 and engages less of the threaded portion 162 of the distal connection portion 150 so the hub 220 and/or distal connection portion 150 are less fully or completely engaged. This relative distal movement or decreased level of engagement causes the projection 212 to apply a smaller force in the proximal direction to the ball valve 190, thereby narrowing the space between the distal wall 130 and the ball valve 190. During this adjustment, the fluid pressure exerted on the ball valve 190 from the distal direction by the flow of the medication of the syringe barrel 300 would increase relative to the force exerted on the ball valve 190 in the distal direction by the projection 212.

In one or more embodiments, the actuator 200 may include a shield (not shown) extending from the distal end 221 of the hub 220 toward the proximal end 219 of the actuator 200. The shield (not shown) may be used to guide the connection between the actuator 200 and the drug delivery connector 100. In one or more embodiments, the shield (not shown) may serve as a guide to facilitate connection of the drug delivery connector and the actuator. In addition, the shield (not shown) may protect the actuator from lateral pressure, which may cause the actuator to break, and/or prevent contamination of the actuator.

In one or more embodiments, the shield (not shown) may be provided in the form of a peripheral wall surrounding the hub 220. The peripheral wall (not shown) may be formed to permit space between the hub and peripheral wall to accommodate any external structures of the syringe barrel 300 and syringe tip. In one or more embodiments, the peripheral wall (not shown) may have a constant cross-sectional width. In a specific embodiment, the peripheral wall (not shown) may have a tapered cross-sectional width increasing from the distal end 221 of the hub 220 to the proximal end 229 of the hub 220. The peripheral wall (not shown) may have an expanded cross-sectional width proximally adjacent to the tapered cross-sectional width. The length of the peripheral wall (not shown) may extend from the distal end 221 of the hub 220 beyond the proximal end 229 of the hub. In one or more embodiments, the length of the peripheral wall (not shown) terminates at the proximal end 219 of the actuator 200. In an alternative embodiment, the length of the peripheral wall (not shown) terminates at the proximal end 229 of the hub 220. In one or more embodiments, the peripheral wall (not shown) may be composed of a clear material so the user may ensure complete connection between the hub 220 and the drug delivery connector 100. The peripheral wall (not shown) may be composed of an extruded or molded plastic material.

In one or more embodiments, a catheter connector 210 is attached to the actuator 200 extends distally from the distal end 211 of the hub 220 and actuator 200. The one or more apertures or open paths 214 of the projection 212 and the open distal end 221 of the hub 220 are in fluid communication with the catheter connector 210. The catheter connector 210 may include a luer lock fitting 230 or a luer slip fitting (not shown) for attachment of the actuator 200 to devices such as catheters, a needle, for example, a spinal needle, an epidural needle, or a hypodermic needle and/or filters, for example, epidural filters.

In one or more embodiments, luer lock fitting 230 of the catheter connector 210 may include an open distal end 231 an open proximal end in fluid communication with the open distal end 221 of the hub 220 and the distal end 211 of the actuator 200. As shown in FIGS. 20-23, the catheter connector 210 may include a tubular body 232 extending from the open distal end 231 to the open proximal end 239. A luer wall 234 may surround the tubular body 232 and form a groove 236 between the tubular body 232 and the luer wall 234. The luer wall 234 may also include an inside surface 237 including a plurality of threads 238 for engaging a catheter, filter or other delivery site.

As shown in FIGS. 21-22, during assembly of the actuator 200 to the drug delivery connector 100 and syringe barrel 300, the proximal end 219 of the actuator 200 is inserted into the passageway 155 of the elongate tube 152 of the distal connection portion 150 of the drug delivery connector. The projection 212 is extended through the bore 132 of the distal wall 130 and enters into the chamber 116. Continuous application of a force on the actuator 200 in the proximal direction, whether or not the force includes rotational forces from the hub 220 being threaded into the threaded portion 162 of the distal connection portion 150, exerts a proximally directed force on the ball valve 190 to release the seal formed between the ball valve 190 and the perimeter 134 of the distal wall 130 at the bore.

In embodiments which utilize a coil spring 192 with the ball valve 190, the actuator 200 exerts a force on the ball valve 190 in the proximal direction that compresses the coil spring 192 and moves the ball valve 190 in a proximal direction away from the distal wall 130. The actuator 200 applies a greater force in the proximal direction on the ball valve 190 to overcome the force exerted on the ball valve 190 by the coil spring 192. In embodiments which utilize a retaining ring 127 on the interior surface 114 of the chamber 116 of the drug delivery connector, the actuator 200 applies a greater force in the proximal direction on the ball valve 190 to overcome the distally directed force exerted on the ball valve 190 by the retaining ring 127. Once the seal between the ball valve 190 and the distal wall 130 is released, fluid communication between the syringe barrel 300, the chamber 116 of the drug delivery connector and the actuator 200 is established and medication can be administered from the syringe barrel 300 and drug delivery connector 100 to the least one aperture or open path 214 of the projection 212 of the actuator 200 to the delivery port.

When the drug delivery connector 100 is coupled with the syringe barrel 300 and actuator 200, the pressurized medication in the syringe barrel 300 and drug delivery connector 100 passes around the ball valve 190 through the bore 132 and distal connection portion 150 of the drug delivery connector. In embodiments which utilize a plurality of ribs 122, one longitudinal protrusion 120 and/or a plurality of longitudinal protrusions 121 on the interior surface 114 of the chamber 116, flow of the medication is facilitated by the flow paths created by ribs 122, longitudinal protrusion 120 and/or plurality of longitudinal protrusions 121, which permit a larger area around the ball valve 190 through which the medication can flow.

The position of the ball valve 190 utilizes the natural flow rate and pressure of the medication contained within the syringe barrel 300 to seal the bore 132 of the drug delivery connector 100. In other devices known in the art, the flow rate and direction of the medication is utilized, at least partially, to open such valves. In embodiments of the present invention, the actuator 200 overcomes the flow rate and direction of the pressurized medication contained within the syringe barrel 300 to release the seal and deliver the medication to an appropriate delivery site. The embodiments described herein, provide an additional safety mechanism by providing a structure that maintains the seal between the chamber 116 of the drug delivery connector that inaccessible until the syringe and drug delivery connector are correctly connected to the appropriate delivery site via the actuator. In addition, the embodiments described herein forces the user to counteract natural forces and enhance the steps required for connection of the syringe barrel to a delivery site, such as a catheter. Moreover, this configuration reduces the possibility of leakage or accidental expulsion of the medication contained in the syringe barrel, before connection to an appropriate delivery site. In addition, the position of the valve in the drug delivery connector and/or the shape of the actuator prevent misconnection or access to delivery sites, such as anesthesia catheter, using IV medication syringes or other syringes that contain other types of medication.

A second aspect of the present invention pertains to a method of administering epidural anesthesia to a catheter connector or other delivery site. In one or more embodiments, the method includes attaching a tip of an empty syringe barrel to an open proximal end of a drug delivery connector as described herein that includes a ball valve for sealing the open distal end of the drug delivery connector. The method further includes attaching a hypodermic needle having a cannula and an opening to the distal end of the drug delivery connector so the opening is in fluid communication with the syringe barrel. In one or more embodiments, the method includes, aspirating an amount of an epidural anesthesia into the syringe barrel through the hypodermic needle and drug delivery connector. The fluid flow of the epidural anesthesia from the hypodermic needle releases the seal between the ball valve and the open proximal end. In one or more embodiments, after a desired amount of epidural anesthesia is aspirated, the method further includes removing the hypodermic needle and attaching the distal end of the drug delivery connector to a catheter connector or other delivery site and expelling the epidural anesthesia from the syringe barrel into the catheter connector or other delivery site. After removal of the hypodermic needle and prior to connection of the drug delivery connector to the catheter connector or other delivery site, the ball valve fluid flow from the syringe barrel exerts a force on the ball valve in the distal direction to cause the ball valve to form a seal with the distal end of to prevent fluid communication between the open distal end and the syringe barrel prior to connection with the catheter connector or other delivery site. In one or more embodiments, the method includes opening the seal formed between the ball valve and the open proximal end. In one or more embodiments, opening the seal includes applying a force on the ball valve in the distal direction. In one or more embodiments, the force is applied to the ball valve in the distal direction by providing an actuator with a free proximal end extending proximally from the actuator and inserting the actuator into the open distal end of the drug delivery connector and attaching the open distal end of the drug delivery connector to the actuator.

In an alternative embodiment, the method of administering epidural anesthesia includes filling a syringe barrel having a tip with a pre-determined amount of epidural anesthesia and attaching the tip of the syringe barrel to an open proximal end of a drug delivery connector, as described herein, including an open distal end and a ball valve for sealing the open distal end. In a specific embodiment, the method may include removing air from within the syringe barrel and drug delivery connector after attachment of the tip to the open proximal end of the drug delivery connector. According to one or more embodiments, the method includes filling the drug delivery connector with the epidural anesthesia to close the ball valve and seal the open distal end. In one or more embodiments, the method includes attaching an actuator in fluid communication to the open distal end of the drug delivery connector. In a specific embodiment, the method includes opening the seal by applying a force in the proximal direction to the actuator to exert a proximally directed force on the ball valve to open the ball valve.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A drug delivery connector comprising:
    a housing including an open distal end, an open proximal end and a chamber within the housing in fluid communication with the open distal end and the open proximal end, the housing including a distal connection portion and a proximal connection portion for attaching the housing to a container;
    a ball valve enclosed within the chamber so that the ball valve floats between the open distal end and the open proximal end in the chamber, wherein the ball valve is moveable in a distal direction to form a releasable seal with the open distal end to prevent fluid flow from the open proximal end to the open distal end upon application of force in the distal direction on the ball valve applied by fluid upon attachment of a container containing the fluid to the proximal connection portion, the ball valve movable in a proximal direction to release the releasable seal to permit fluid flow from the open proximal end to the open distal end;

an actuator for attachment to the open distal end of the housing, the actuator comprising an open distal end and a projection extending in the proximal direction and including at least one aperture in fluid communication with the open distal end of the actuator and the open distal end of the housing; and a structure that forms one or more fluid flow paths around the ball valve selected from one or more of a longitudinal protrusion, a rib, an expanding sidewall and combinations thereof.

2. The drug delivery connector of claim 1, wherein the housing comprises a proximal wall disposed adjacent to the open proximal end, the proximal wall including at least one aperture allowing constant fluid communication between the open proximal end and the chamber.

3. The drug delivery connector of claim 1, wherein the housing comprises a distal wall disposed adjacent to the open distal end, the distal wall including a bore having a perimeter, the perimeter configured to contact the ball valve to form a releasable seal between the ball valve and the distal wall.

4. The drug delivery connector of claim 1, wherein the distal connection portion comprises a luer lock fitting.

5. The drug delivery connector of claim 1, wherein the proximal connection portion comprises a luer lock fitting.

6. The drug delivery connector of claim 1, wherein upon attachment of the actuator to the open distal end of the housing, the projection applies a force on the ball valve in the proximal direction to move the ball valve in the proximal direction.

7. A drug delivery connector comprising a housing including an open distal end, an open proximal end and a chamber within the housing in fluid communication with the open distal end and the open proximal end, the housing including a distal connection portion and a proximal connection portion for attaching the housing to a container;

a ball valve enclosed within the chamber so that the ball valve floats between the open distal end and the open proximal end in the chamber, wherein the ball valve is moveable in a distal direction to form a releasable seal with the open distal end to prevent fluid flow from the open proximal end to the open distal end upon application of force in the distal direction on the ball valve applied by fluid upon attachment of a container containing the fluid to the proximal connection portion, the ball valve movable in a proximal direction to release the releasable seal to permit fluid flow from the open proximal end to the open distal end; and an actuator for attachment to the open distal end of the housing, the actuator comprising an open distal end and a projection extending in the proximal direction and including at least one aperture in fluid communication with the open distal end of the actuator and the open distal end of the housing;

wherein the housing comprises a retaining ring that inhibits movement of the ball valve in the proximal direction.

8. The drug delivery connector of claim 7, wherein the ball valve is movable in the proximal direction upon application of force in the proximal direction on the ball valve by the actuator, the force of the actuator being sufficient to overcome a distally directed force exerted on the ball valve by the retaining ring.

9. The drug delivery connector of claim 7, wherein the housing comprises a proximal wall disposed adjacent to the open proximal end, the proximal wall including at least one aperture allowing constant fluid communication between the open proximal end and the chamber.

10. The drug delivery connector of claim 7, wherein the housing comprises a distal wall disposed adjacent to the open distal end, the distal wall including a bore having a perimeter, the perimeter configured to contact the ball valve to form a releasable seal between the ball valve and the distal wall.

11. The drug delivery connector of claim 7, wherein the distal connection portion comprises a luer lock fitting.

12. The drug delivery connector of claim 7, wherein the proximal connection portion comprises a luer lock fitting.

13. The drug delivery connector of claim 7, wherein upon attachment of the actuator to the open distal end of the housing, the projection applies a force on the ball valve in the proximal direction to move the ball valve in the proximal direction.

* * * * *